(12) United States Patent
Bontus et al.

(10) Patent No.: US 7,889,901 B2
(45) Date of Patent: Feb. 15, 2011

(54) COMPUTED TOMOGRAPHY METHOD WITH HELICAL RELATIVE MOVEMENT AND CONICAL BEAM BUNDLE

(75) Inventors: Claas Bontus, Hamburg (DE); Michael Grass, Buchholz in der Nordheide (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 858 days.

(21) Appl. No.: 11/815,606

(22) PCT Filed: Jan. 31, 2006

(86) PCT No.: PCT/IB2006/050332

§ 371 (c)(1),
(2), (4) Date: Aug. 6, 2007

(87) PCT Pub. No.: WO2006/085242

PCT Pub. Date: Aug. 17, 2006

(65) Prior Publication Data

US 2008/0205727 A1     Aug. 28, 2008

(30) Foreign Application Priority Data

Feb. 10, 2005   (EP) .................................. 05100965

(51) Int. Cl.
*G06K 9/00* (2006.01)
*A61B 6/00* (2006.01)

(52) U.S. Cl. ............................ 382/128; 382/274; 378/4

(58) Field of Classification Search ................. 382/100, 382/128, 129, 130, 131, 132, 133, 134, 154, 382/168, 173, 181, 220, 232, 254, 260, 274, 382/288, 289, 291, 296, 305, 312; 378/15, 378/4, 21, 8, 207, 206
See application file for complete search history.

(56) References Cited

U.S. PATENT DOCUMENTS

| 5,515,409 | A  | * | 5/1996 | Hsieh ........................... 378/15 |
| 6,139,183 | A  | * | 10/2000 | Graumann ................... 378/206 |
| 6,289,074 | B1 | * | 9/2001 | Arai et al. ....................... 378/4 |
| 6,491,430 | B1 | * | 12/2002 | Seissler ...................... 378/207 |
| 7,526,062 | B2 | * | 4/2009 | Manzke et al. ................. 378/8 |
| 2003/0142778 | A1 | * | 7/2003 | Proksa ........................... 378/4 |

OTHER PUBLICATIONS

Bontus, C., et al.; A quasiexact reconstruction algorithm for helical CT using a 3-Pi acquisition; 2003; Am. Assoc. Phys. Med.; 30(9)2493-2502.

(Continued)

*Primary Examiner*—Seyed Azarian

(57) ABSTRACT

The invention relates to a computed tomography method in which a periodically moving object is irradiated by a conical beam bundle. An nPi-relative movement is generated between a radiation source, which generates the conical beam bundle, and the object. During the nPi-relative movement, measured values are acquired, which depend on the intensity in the beam bundle on the other side of the object and from these measured values filter values are determined, which are divided into different groups. The filter values of at least one group are weighted in dependence on the movement of the object, wherein, when filter values of several groups are weighted, filter values of different groups are weighted differently in dependence on the movement of the object. Finally, a CT image of the object is reconstructed from the filter values.

16 Claims, 11 Drawing Sheets

OTHER PUBLICATIONS

Figure 1:
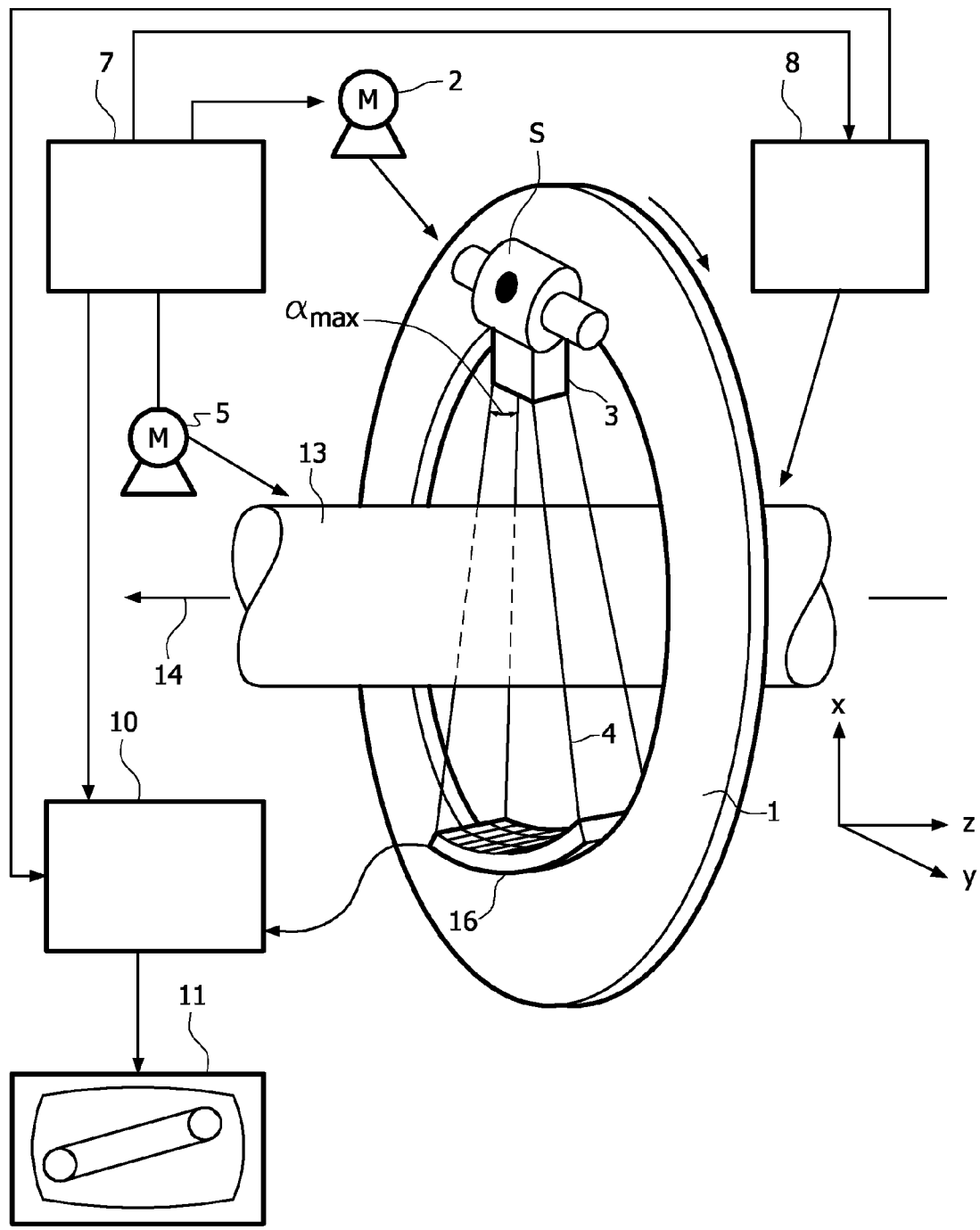

Bontus, C., et al.; EnPiT: A reconstruction algorithm for helical CT; 2004; IEEE Nuclear Science Symposium record; vol. 5; pp. 3027-3030.

Kachelriess, M., et al.; Kymogram detection and kymogram-correlated image reconstruction from subsecond spiral computed tomography scans of the heart; 2002; Medical Physics; 29(7)1489-1503.

Katsevich, A.; Analysis of an exact inversion algorithm for spiral cone-beam CT; 2002; Phys. Med. Biol.; 47(15) 2583-2597.

Manzke, R., et al.; Adaptive temporal resolution optimization in helical cardiac cone beam CT reconstruction; 2003; Med. Phys.; 30(121)3072-3080.

Manzke, R., et al.; Automatic phase determination for retrospectively gated cardiac CT; 2004; Med. Phys.; 31(12) 3345-3362.

\* cited by examiner

COMPUTED TOMOGRAPHY METHOD WITH HELICAL RELATIVE MOVEMENT AND CONICAL BEAM BUNDLE

The invention concerns a computed tomography method, in which an examination zone in which there is arranged a periodically moving object is irradiated along a helical trajectory by a conical beam bundle. The invention also relates to a computer tomograph for carrying out the method according to the invention and to a computer program for controlling the computer tomograph.

Methods of the kind mentioned initially are often used in examinations of the heart and are described, for example, in "Multislice CT in Cardiac Imaging: Technical Principles, Imaging Protocols, Clinical Indications and Future Perspective", B. M. Ohnesorge et al., Springer Verlag, 2002, ISBN 3540429662. In these methods, measured values are acquired with a detector unit, the cardiac motion being recorded by means of an electrocardiograph during measuring. The measured values are weighted in dependence on the cardiac motion, and a computed tomography image (CT image) of the heart is reconstructed from the weighted measured values.

The drawback of these known methods is that, despite the weighting, the reconstructed CT images contain artifacts owing to the movement of the object, which diminish the image quality.

It is an object of the invention to specify a computed tomography method of the kind mentioned initially in which the quality of the reconstructed CT image is enhanced.

That object is achieved in accordance with the invention by a computed tomography method having the following steps:

a) generation with a radiation source of a conical beam bundle passing through an examination zone and a periodically moving object located therein, b) generation of a nPi-relative movement between the radiation source on the one hand and the examination zone on the other hand, which comprises a rotation about an axis of rotation and a displacement in a displacement direction parallel to the axis of rotation and takes the form of a helix, c) acquisition by means of the detector unit, during the nPi-relative movement, of measured values that are dependent on the intensity in the beam bundle on the other side of the examination zone, d) determination of filter values by filtering the measured values and dividing the filter values into different groups, e) weighting of the filter values of at least one group in dependence on the movement of the object, wherein, when filter values of several groups are weighted, filter values of different groups are differently weighted in dependence on the movement of the object, f) reconstruction of a CT image of the examination zone from the filter values.

The nPi-relative movement and also the nPi-acquisition, that is, the acquisition of measured values during an nPi-relative movement, are generally well known. With this specific relative movement, the pitch, that is, the spacing of adjacent turns of the helical trajectory, is selected so that from each radiation source position, n+1 turns are projected onto the detector surface, n being a natural, odd number greater than 1. As a rule, one talks of the 3Pi-, 5Pi-, 7Pi- etc. relative movement or acquisition. The projections of the turns of the helical trajectory onto the detector surface are known as mPi-boundary lines, with m=1, 3, ..., n. The two innermost projected turns are the Pi-boundary lines, the two projected turns each adjacent to a Pi boundary line are the 3Pi-boundary lines, the 5Pi-boundary lines come next, and so on. The course of the mPi-boundary lines on the detector surface is explained more precisely below.

In contrast to the prior art mentioned initially, not all measured values are weighted in equal measure in dependence on the object movement; on the contrary, the measured values are filtered, and the resulting filter values are divided into groups, at least one group of filter values being weighted in dependence on the object movement. If filter values of several groups are weighted, then filter values of different groups are filtered differently in dependence on the object movement, that is, filter values of a group that have been formed by filtering measured values that have been acquired during a specific movement phase of the object are weighted differently, for example, multiplied by a larger or smaller weighting factor, from filter values of another group that have been formed by filtering measured values that have been acquired during the same movement phase of the object. This group-dependent weighting enables filter values which, were they to be weighted in dependence on the object movement, would not contribute to enhancement of the image quality or would impair the image quality, to be weighted more weakly than other filter values or not at all in dependence on the object movement. In this way, the image quality is improved compared with the methods mentioned initially.

In the embodiment as claimed in claim 2, the filter values are back-projected, which leads to a good image quality of the reconstructed object for little computation effort.

According to claim 3, the measured values are filtered by means of a κ-filter, which is explained in detail below. The use of a κ-filter and also the derivation of the measured values as claimed in claim 4 before filtering lead to a further improvement in image quality.

According to claim 5, in step d) the filter values are filtered by filtering the measured values in such a manner and dividing the filter values into groups in such a manner that filter values of different groups comprise contributions of radon planes that intersect the helix with varying frequency. That is to say, the filter values of one group comprise, for example, contributions of radon planes that intersect the helix 1 to 3 times, the filter values of another group comprise, for example, contributions of radon planes that intersect the helix 4 to 6 times, and the filter values of another group comprise, for example, contributions of radon planes that intersect the helix more than 6 times.

The embodiment as claimed in claim 5 and also the embodiment as claimed in claim 6 lead to a further improvement in image quality.

According to claim 7, first filter values are determined, which comprise contributions of radon planes that intersect the helix at least n times, and second filter values are determined, which comprise contributions of radon planes that intersect the helix fewer than n times. The filter values are then divided into different groups, such that the first filter values form a first group and the second filter values form a second group. In step e), the filter values of the first group are then weighted more heavily in dependence on the object movement than the filter values of the second group. For example, in dependence on the object movement, only the first filter values are weighted and not the second filter values, whereby the image quality of the reconstructed CT image is further enhanced.

Inter alia, a filter value of one group is weighted more heavily in dependence on the object movement than a filter value of a different group, if a filter value of the one group is multiplied by a larger weighting factor than a filter value of the other group, although both filter values have been determined by filtering measured values that have been acquired while the object was in the same phase of movement. The fact that the filter values of one group are weighted more heavily in dependence on the object movement than the filter values of a different group includes also the case that the filter values of the one group are weighted, even if only weakly, in dependence on the object movement, and the filter values of the other group are not weighted in dependence on the object movement.

Radon planes are known, for example, from "The Mathematics of Computerized Tomography", F. Natterer, Wiley, New York, 1986, so that more specific details of the course of radon planes and their significance for the reconstruction of computed tomography images are not given.

Claim 8 describes a relatively simple manner of determining first filter values comprising contributions of radon planes that intersect the helix at least n times, and second filter values comprising contributions of radon planes that intersect the helix fewer than n times.

The embodiments of the computed tomography method according to the invention described in claims 9 to 13 further enhance the quality of the reconstructed CT image.

Claims 14 and 15 describe a computer tomograph for carrying out the method according to the invention. Claim 16 defines a computer program for controlling a computer tomograph as claimed in claim 14.

These and other aspects of the invention are apparent from and will be elucidated with reference to the embodiments described hereinafter.

Figure 2:
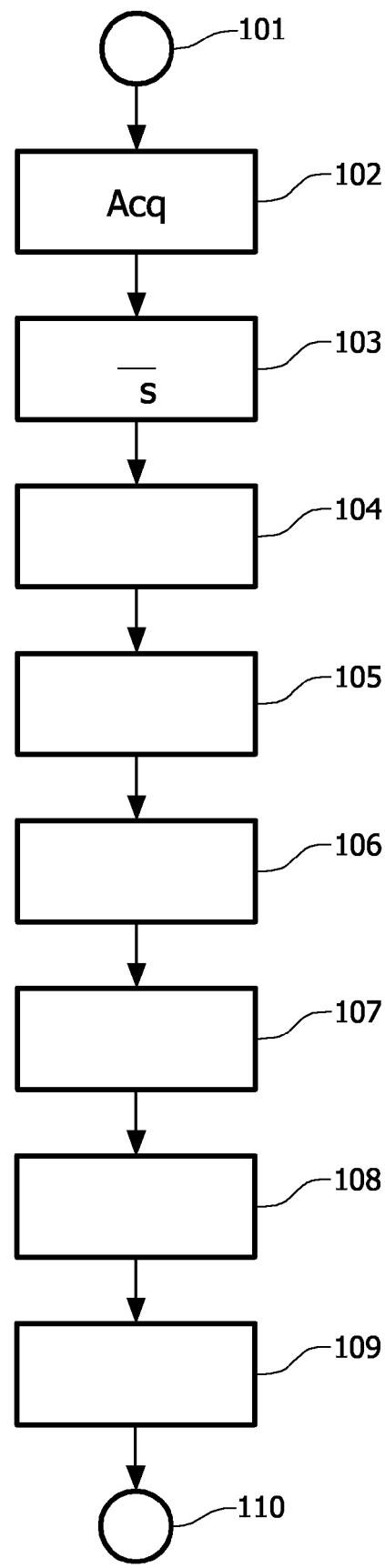
Figure 3:
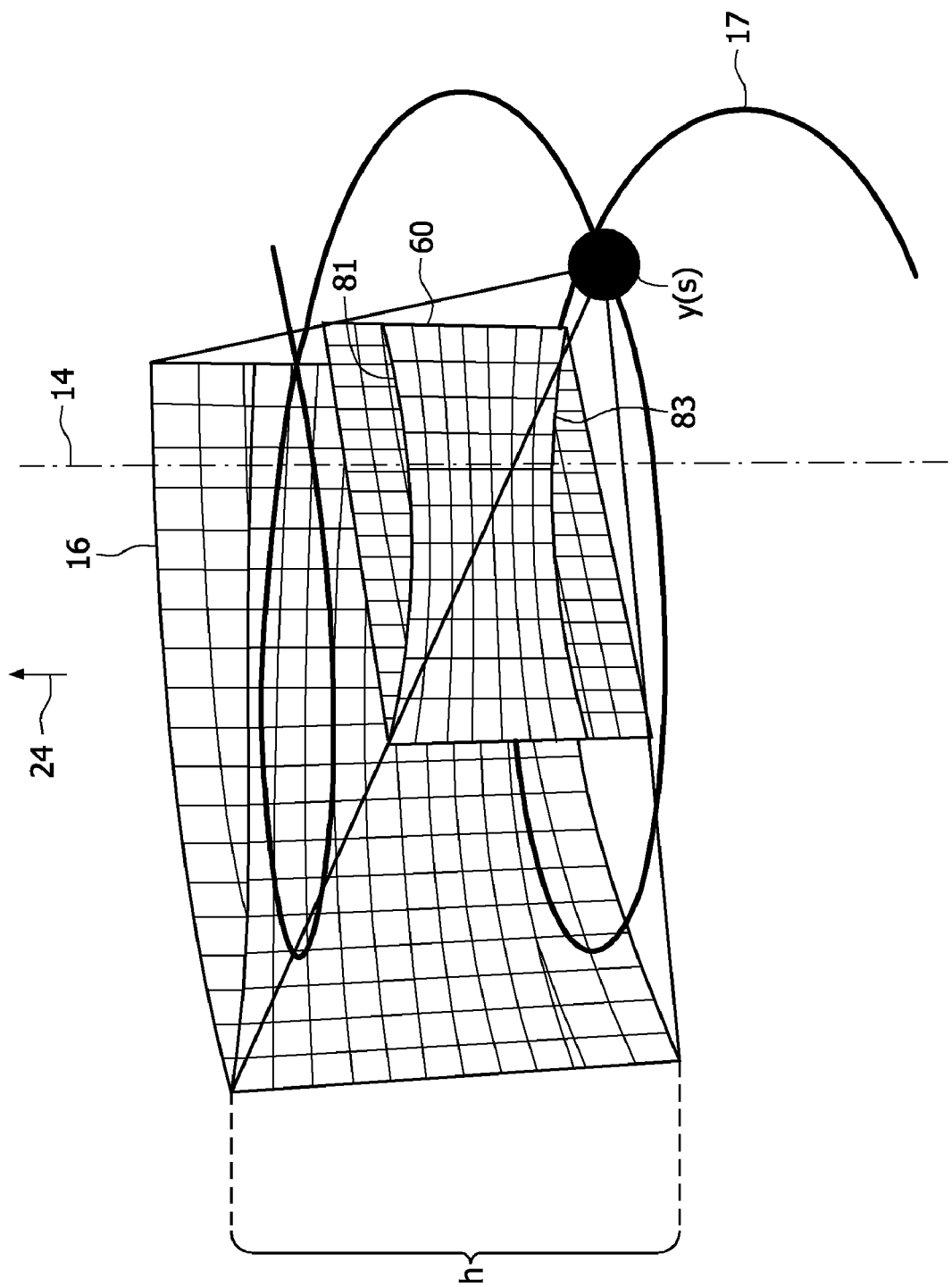
Figure 4:
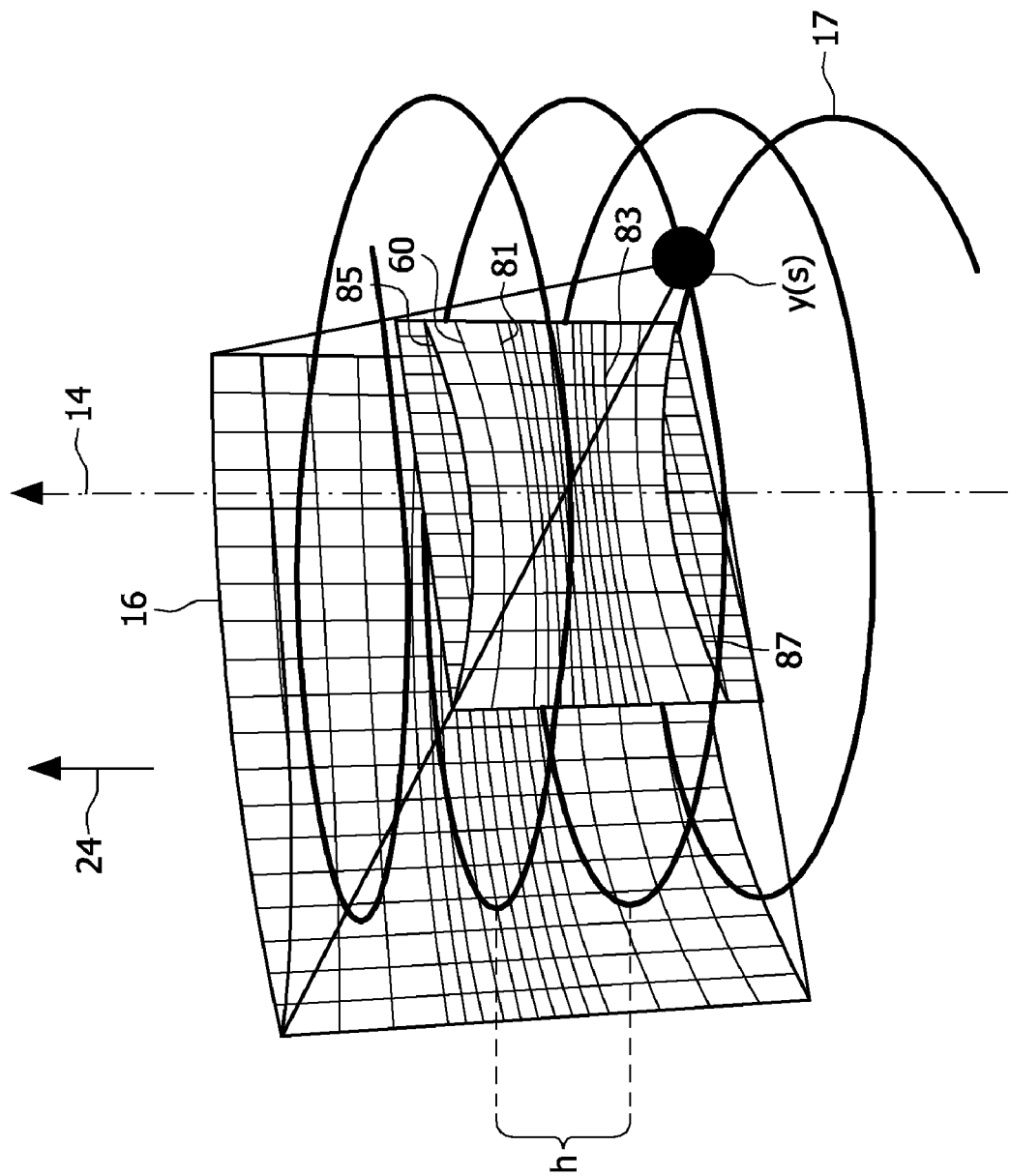
Figure 5:
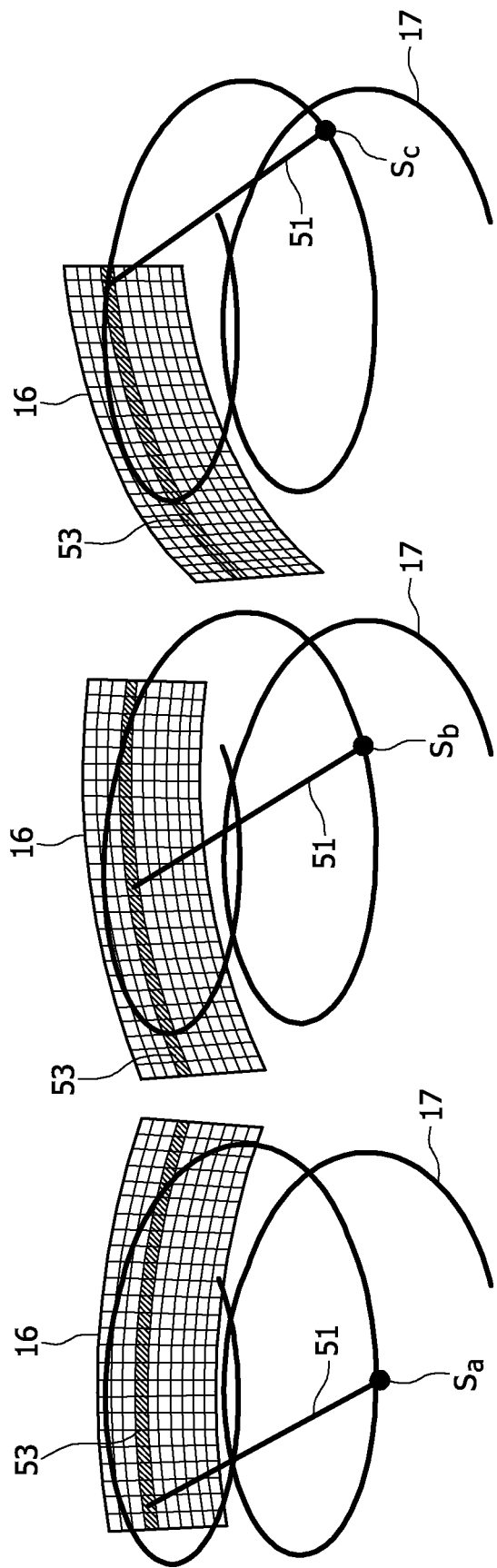
Figure 6:
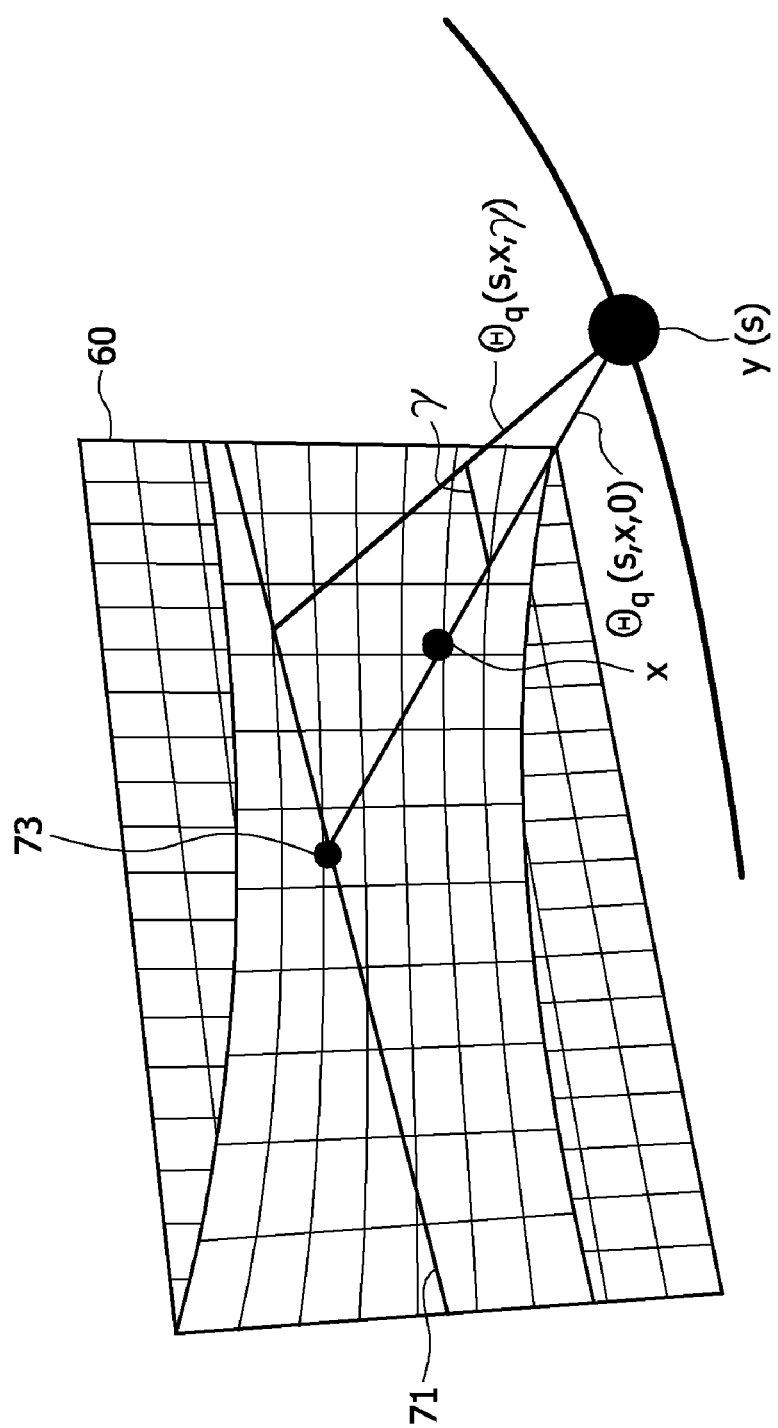
Figure 7:
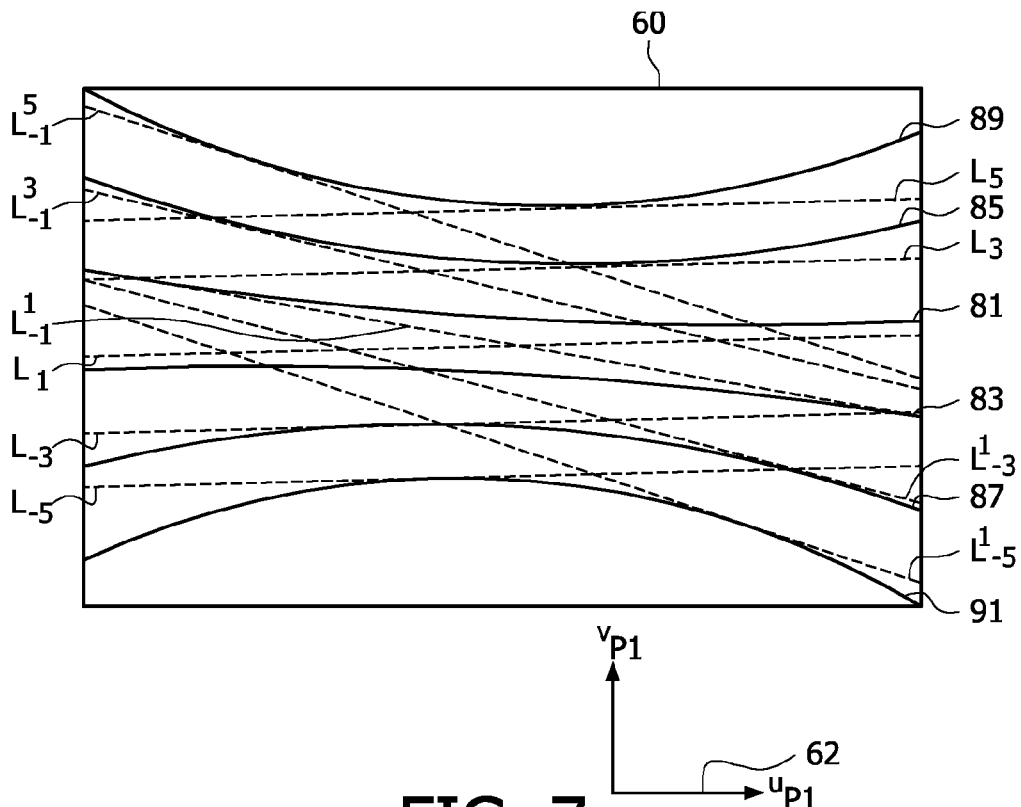
Figure 8:
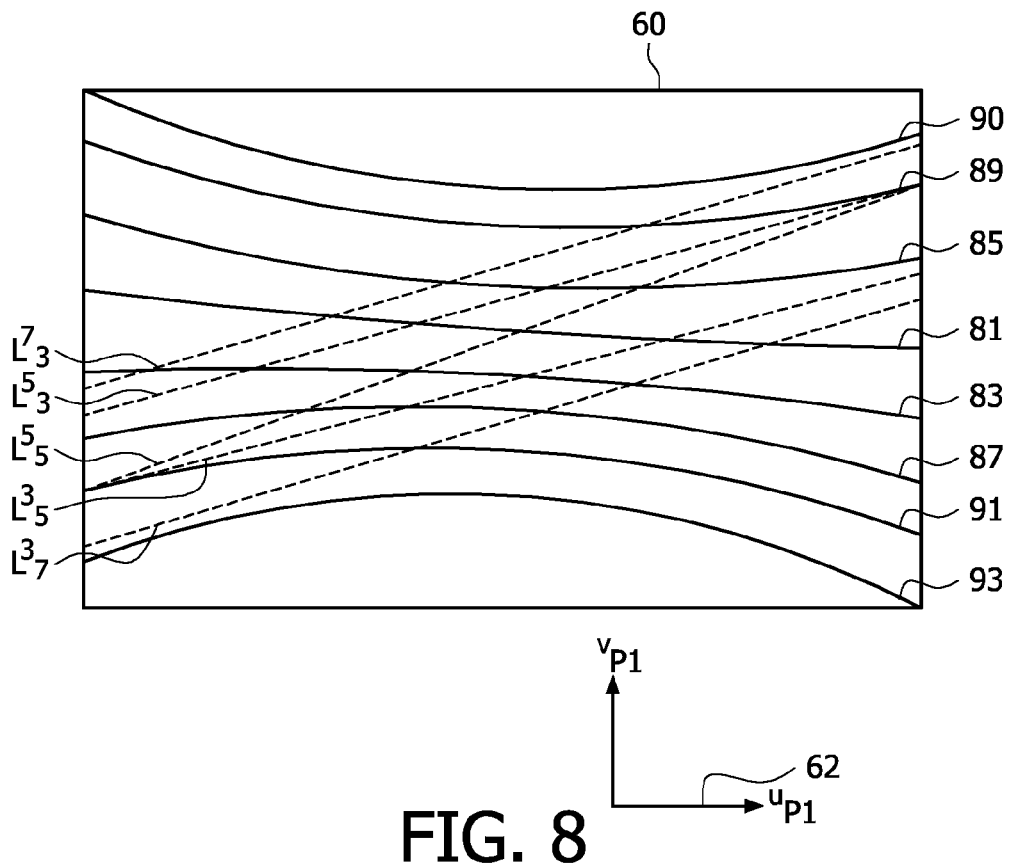
Figure 13:
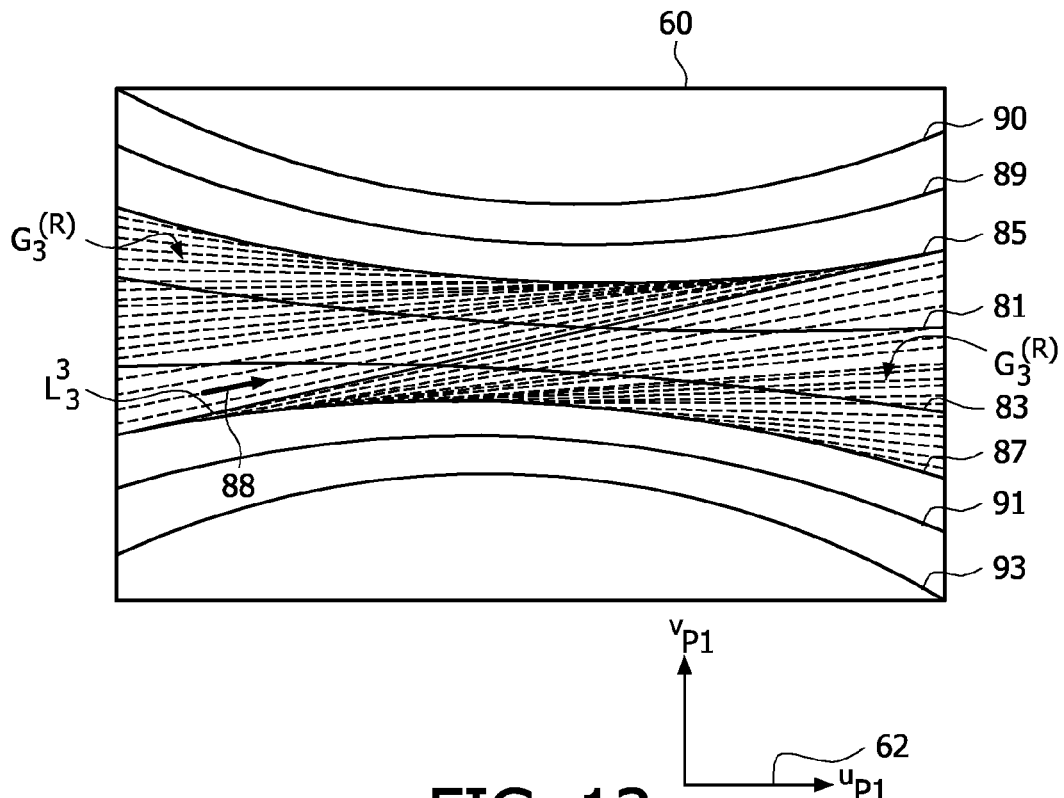
Figure 14:
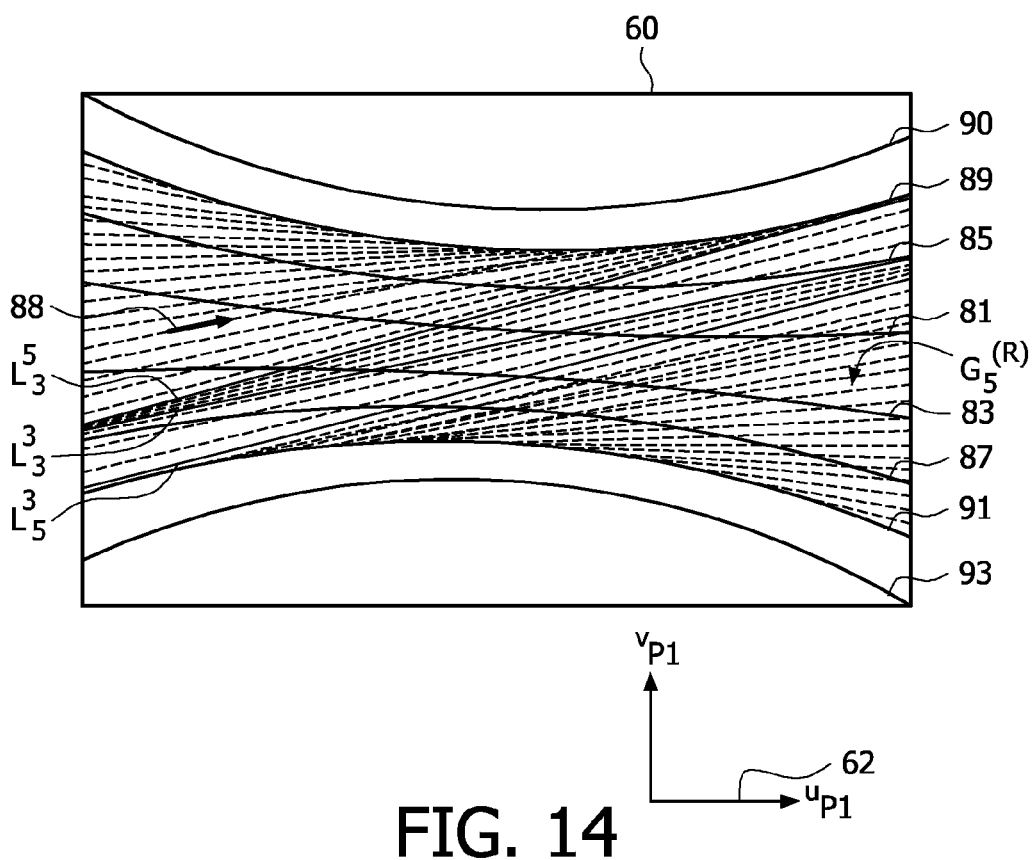
Figure 15:
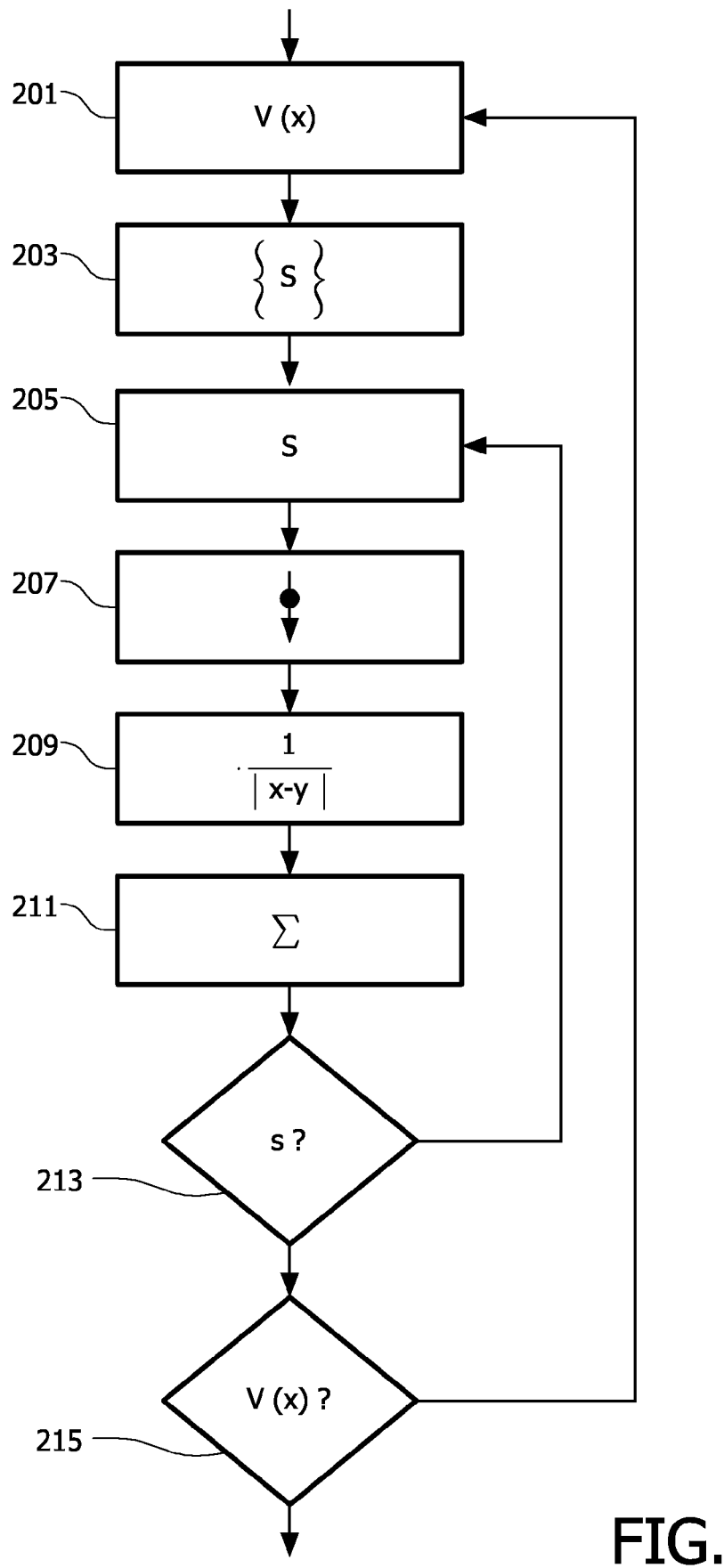

In the drawings:

FIG. 1 shows a computer tomograph, with which the method according to the invention can be implemented, FIG. 2 is a flow chart of the method according to the invention, FIG. 3 is a perspective view of a helical trajectory, a radiation source, a focus-centered and a planar detector surface in the case of a Pi-relative movement, FIG. 4 is a perspective view of a helical trajectory, a radiation source, a focus-centered and a planar detector surface during a 3Pi-relative movement, FIG. 5 is a perspective view of parallel rays that emanate from different radiation source positions and are incident on the same row of detectors, FIG. 6 is a perspective view of a portion of the helical trajectory, the radiation source, and the planar detector surface, FIG. 7 shows the course of mPi-boundary lines and dividing lines on the planar detector surface during a 5Pi-relative movement, FIG. 8 shows the course of mPi-boundary lines and dividing lines on the planar detector surface during a 7Pi-relative movement, FIG. 9 to FIG. 12 show a course of filter lines during a 5Pi-relative movement, FIG. 13 and FIG. 14 show a course of filter lines during a 7Pi-relative movement, and FIG. 15 shows a flow chart of a filtered back-projection.

The computer tomograph illustrated in FIG. 1 comprises a gantry 1, which is capable of rotating about an axis of rotation 14 running parallel to the z-direction of the co-ordinate system illustrated in FIG. 1. For that purpose, the gantry 1 is driven by a motor 2 at a preferably constant but adjustable angular velocity. A radiation source S, for example an X-ray tube, is fixed to the gantry 1. The X-ray tube is provided with a collimator arrangement 3, which from the radiation produced by the radiation source S extracts a conical beam bundle 4, i.e. a beam bundle that has a finite extent other than zero both in the z-direction and in a direction perpendicular thereto (i.e. in a plane perpendicular to the axis of rotation).

The beam bundle 4 passes through a cylindrical examination zone 13, in which a periodically moving object (not illustrated) is located. In this exemplary embodiment this object is a beating heart, which performs proper motion and is possibly additionally moved back and forth by respiratory motion of the patient. In other embodiments, other periodically moving body organs, such as the liver or the brain, periodically moving parts of body organs or periodically moving technical objects could alternatively be irradiated.

After passing through the examination zone 13, the beam bundle 4 is incident on a detector unit 16 fixed to the gantry 1, the detector unit having a detector surface comprising a plurality of detector elements, which in this embodiment are arranged matrix-form in rows and columns. The detector columns extend parallel to the axis of rotation 14. The detector rows are located in planes perpendicular to the axis of rotation, in this embodiment on an arc of a circle around the radiation source S (focus-centered detector surface). In other embodiments they could alternatively be of a different form, for example, they could describe an arc of a circle about the axis of rotation 14 or be linear. Each of the detector elements on which the beam bundle 4 is incident supplies in each position of the radiation source a measured value for a beam from the beam bundle 4.

The angle of aperture of the beam bundle 4 denoted by $\alpha_{max}$ determines the diameter of the object cylinder, within which the object to be examined is located during acquisition of the measured values. The angle of aperture is here defined as the angle that a ray lying in a plane perpendicular to the axis of rotation 14 at the edge of the beam bundle 4 encloses with a plane defined by the radiation source S and the axis of rotation 14.

The examination zone 13, or rather the object or the patient support table, can be displaced by means of a motor 5 parallel to the axis of rotation 14 and the z-axis. Alternatively and equivalently, the gantry could be displaced in that direction. If the object is a technical object and not a patient, the object can be rotated during an examination, while the radiation source S and the detector unit 16 remain stationary.

If the motors 2 and 5 run simultaneously, the radiation source S and the detector unit 16 describe a helical trajectory relative 17 to the examination zone 13. If, however, the motor 5 for advance in the direction of the axis of rotation 14 is idle, and the motor 2 allows the gantry to rotate, a circular trajectory is produced for the radiation source S and the detector unit 16 relative to the examination zone 13. Only the helical trajectory will be considered below.

The helical trajectory 17 may be parameterized by $$y(s) = \begin{pmatrix} R\cos s \\ R\sin s \\ s\frac{h}{2\pi} \end{pmatrix} \quad (1)$$

wherein R is the radius of the helical trajectory 17, s is the angular position on the helical trajectory and h is the pitch, that is, the spacing between two adjacent turns of the helical trajectory.

During acquisition of the measured values, the cardiac motion is recorded in known manner by means of an electrocardiograph 8. For that purpose, the thoracic region of a patient is connected by means of electrodes (not illustrated) to the electrocardiograph 8. In other embodiments, especially in the case of other moving objects, the movement of the object can be followed in other known manners. Thus, for example, movement information can be obtained from the values measured by the detector unit 16, so that detection of the movement with an additional device, such as an electrocardiograph, could be omitted. For that purpose, first of all the measured values are used to prepare a kymogram, from which in known manner the movement can be derived. A detailed description of this method can be found in "Kymogram detection and kymogram-correlated image reconstruction from subsecond spiral computed tomography scans of the heart", M. Kachelrieβ, D. A. Sennst, W. Maxlmoser, W. A. Kalender, Medical Physics 29(7):1489-1503, 2002, to which reference is hereby made.

In the present embodiment, it is assumed that the patient is not breathing during the measurement. The respiratory motion can therefore be disregarded. In other embodiments, the respiratory motion could be measured, for example, using a deformable abdominal belt that is connected to a respiratory motion-measuring device.

The measured values acquired by the detector unit 16 are fed to a reconstruction and image-processing computer 10, which is connected to the detector unit 16, for example, via a contactlessly operating data transmission (not illustrated). In addition, the electrocardiogram is transmitted from the electrocardiograph 8 to the reconstruction and image-processing computer 10. The reconstruction and image-processing computer 10 reconstructs the absorption distribution in the examination zone 13 and reproduces it, for example, on a monitor 11. The two motors 2 and 5, the reconstruction and image-processing computer 10, the radiation source S, the electrocardiograph 8, and the transfer of the measured values from the detector unit 16 to the reconstruction and image-processing computer 10 are controlled by the control unit 7. The control unit 7 also controls the transmission of the electrocardiogram from the electrocardiograph 8 to the reconstruction and image-processing computer 10.

In other embodiments, the acquired measured values and the measured electrocardiograms for reconstruction can first be fed to one or more reconstruction computers, which forward the reconstructed data, for example, via a fiber optic cable, to an image-processing computer.

The individual steps of one embodiment of the computed tomography method according to the invention are explained in the following with reference to the flow chart in FIG. 2.

After initialization in step 101, the gantry rotates at an angular velocity that in this example of embodiment is constant. It may also vary however, for example, as a function of time or of radiation source position.

In step 102, the examination zone is displaced parallel to the axis of rotation 14 in displacement direction 24 (opposite to the direction of the z-axis of the system of co-ordinates in FIG. 1), for example by displacing the patient support table, and the radiation of the radiation source S is switched on, so that the detector unit 16 is able to detect the radiation from a plurality of angular positions s and the radiation source S moves relative to the examination zone 13 on the helical trajectory 17. At the same time, or alternatively even before the radiation source S is switched on, the electrocardiograph 8 is activated, so that an electrocardiogram is measured simultaneously.

The pitch h is here selected in such a way that for each radiation source position y(s) at least four adjacent turns of the helical trajectory 17 along the rays that issue from the respective radiation source position y(s) are projected onto the detector surface. If four turns are projected on the onto detector surface, then this is a 3Pi-acquisition or 3Pi-relative movement (FIG. 4). If n+1 turns are projected onto the detector surface, wherein n is an odd integer greater than or equal to 3, then the acquisition is known as nPi-acquisition and the relative movement as nPi-relative movement.

The course of the projection of individual turns onto a notional, planar detector surface 60, the surface normal of which passes through the respective radiation source position y(s) and which contains the axis of rotation 14, can be described by the following equations:

$$v_{P1}(u_{P1}) = +\frac{h}{2\pi}\left(1 + \left(\frac{u_{P1}}{R}\right)^2\right)\left(m\frac{\pi}{2} - \arctan\frac{u_{P1}}{R}\right) \text{ and} \quad (2)$$

$$v_{P1}(u_{P1}) = -\frac{h}{2\pi}\left(1 + \left(\frac{u_{P1}}{R}\right)^2\right)\left(m\frac{\pi}{2} + \arctan\frac{u_{P1}}{R}\right). \quad (3)$$

In these equations, $u_{P1}$, and $v_{P1}$ are co-ordinates of a Cartesian system of co-ordinates 62 on the planar detector surface 60, wherein the $u_{P1}$-co-ordinate axis is oriented perpendicular and the $v_{P1}$-co-ordinate axis is oriented parallel to the axis of rotation 14 in the displacement direction 24. For reasons of clarity, this co-ordinate system 62 is illustrated in FIGS. 7 to 14 below the planar detector surface 60. The origin of the co-ordinate system 62 lies at the center of the detector surface 60 however. The size of the planar detector surface 60 is chosen so that all rays that are incident upon the focus-centered detector surface 16 also pass through the planar detector surface 60.

The relationship of the co-ordinates on the notional, planar detector surface 60 to the co-ordinates of the real, focus-centered detector surface 16 is given by the following equations:

$$u_{P1} = R\tan\beta \text{ and} \quad (4)$$

$$v_{P1} = \sqrt{R^2 + u_{P1}^2}\,\tan\lambda = R\frac{\tan\lambda}{\cos\beta} = \frac{v_F}{\cos\beta}\frac{R}{D}. \quad (5)$$

Here, λ is the cone angle of a beam coming from y(s), that is, the angle that this beam encloses with a plane perpendicular to the axis of rotation 14 and containing the radiation source position y(s). Furthermore, β is the fan angle of a beam coming from y(s), that is, the angle that the projection of this beam onto a plane oriented perpendicular to the axis of rotation 14 and containing the radiation source position y(s) encloses with a line passing through the radiation source position y(s) and oriented perpendicular to the axis of rotation 14. The variable D denotes the distance of the radiation source position y(s) from the middle of the focus-centered, real detector surface 16.

During the Pi-acquisition, only two turns adjacent to the respective radiation source position y(s), are projected onto the real, focus-centered detector surface 16 and onto the notional, planar detector surface 60. The course 81 of the upper projection in FIG. 3 onto the planar detector surface 60 is described by equation (2), whilst the course 83 of the lower projection in FIG. 3 onto the planar detector surface 60 is described by equation (3) (in each case with m=1). The upper projection is referred to below as the upper Pi-boundary line 81 and the lower projection is referred to below as the lower Pi-boundary line 83.

The terms "upper", "lower", "left" and "right" and similar expressions relate within the scope of the invention to the orientation of the planar detector surface 60 and the associated system of co-ordinates 62, as they are illustrated in FIGS. 3, 4 and 7 to 14. Thus, the displacement direction 24 and the $v_{P1}$-co-ordinate axis point "upwards". Furthermore, the $u_{P1}$-co-ordinate axis points "to the right".

During the 3Pi-acquisition, four adjacent turns are projected onto the real, focus-centered detector surface 16 and onto the notional, planar detector surface 60. The course of the uppermost projection 85 in FIG. 4 onto the planar detector surface 60 is described by equation (2), whilst the course of the lowermost projection 87 in FIG. 4 onto the planar detector surface 60 is described by equation (3) (in each case with m=3). The uppermost projection is referred to below as the upper 3Pi-boundary line 85 and the lowermost projection is referred to below as the lower 3Pi-boundary line 87. During the 3Pi-acquisition, an upper Pi-boundary line 81 and a lower Pi-boundary line 83 and an upper 3Pi-boundary line 85 and a lower 3Pi-boundary line 87 run onto the detector surface.

During an nPi-acquisition, upper Pi-3Pi-, 5Pi-, . . . , nPi-boundary lines (as per equation (2)) and lower Pi-3Pi-, 5Pi-, . . . , nPi-boundary lines (as per equation (3)) run accordingly onto the planar detector surface 60.

Upper Pi-3Pi-, 5Pi- etc. boundary lines have positive $v_{P1}$-co-ordinates on the planar detector surface, whereas lower Pi-, 3Pi-, 5Pi- etc. boundary lines have negative $v_{P1}$-co-ordinates.

During a 3Pi-acquisition, as is illustrated in FIG. 4, h=57.6 mm can be chosen as the pitch when the fan angle of the beam that inclines most strongly out of a plane containing the axis of rotation 14 and the radiation source position y(s) amounts to 52.1°, and when the acquisition geometry is additionally distinguished by an expansion of the real, focus-centered detector 16 in the direction of the axis of rotation 14 of 175.1 mm, a spacing of the beam source position y(s) from the axis of rotation 14 of 570 mm and a spacing of the radiation source position y(s) from the center of the real, focus-centered detector surface 16 of 1040 mm.

In step 103, the measured values are derived in accordance with the following equation partially in conformity with s, that is, in conformity with the angular position of the radiation source S:

$$D'_f(y(s), \Theta) = \frac{\partial D_f(y(s), \Theta = \text{const.})}{\partial s} \text{ with} \quad (6)$$

$$D_f(y(s), \Theta) = \int_0^\infty dl f(y + l\Theta). \quad (7)$$

Here, $\Theta$ is a unit vector that differentiates measured values, which, although they have been caused by beams coming from the same radiation source position, are incident upon different detector elements. The unit vector $\Theta$ thus specifies the direction of the beam belonging to the measured value. The direction of the unit vector, that is, the direction of a beam, can be parameterized by the angular position s of the radiation source on the helical trajectory 17 and by a point x in the examination zone 13 through which the beam runs ($\Theta=\Theta(s, x)$). Furthermore, $D_f(y(s), \Theta)$ describes the measured value for a specific radiation source position y(s) and a specific ray direction $\Theta$ that has been measured with the focus-centered detector after the corresponding ray has passed with the absorption distribution f(x) through the object to be reconstructed.

In the case of the partial derivation of the measured values in conformity with equation (6), it should be noted that $\Theta$ remains constant, so that, for the derivation, in each case measured values of parallel rays have to be taken into account.

Since parallel rays have the same cone angle, in the case of the focus-centered detector surface 16 used here, parallel rays 51 are incident on the same detector row 53 (see FIG. 5, in which only a partial area of the detector surface 16 is illustrated). For partial derivation, the measured values can therefore initially be re-sorted. For that purpose, measured values that belong to parallel rays 51, that is, to the same detector row 53 but to different angular positions $s_a$, $s_b$, $s_c$ of the radiation source, are in each case combined into one quantity. The measured values of each quantity are then derived, for example, numerically using the known finite element method in conformity with the angular position s of the radiation source, wherein known smoothing techniques can be used.

In step 104, the derived measured values are projected along their rays onto the notional, planar detector surface 60.

In step 105, one or more filter lines are assigned to each measured value, each filter line in turn being assigned to a filter direction. The filter lines and filter directions indicate which measured values are taken into account in what sequence according to the following equation, in order to obtain a first filter value $P_g(s, x)$ and/or a second filter value $P_{ug}(s, x)$ for a measured value to be filtered, the ray of which, starting from the radiation source position y(s), passes through the point x in the examination zone:

$$P_g(s, x) = \sum_{q=1}^{N_g} \mu_{q,g} \int_{-\pi}^{\pi} \frac{d\gamma}{\sin\gamma} D'_f(y(s), \Theta_{q,g}(s, x, \gamma)) \text{ and} \quad (8)$$

$$P_{ug}(s, x) = \sum_{q=1}^{N_{ug}} \mu_{q,ug} \int_{-\pi}^{\pi} \frac{d\gamma}{\sin\gamma} D'_f(y(s), \Theta_{q,ug}(s, x, \gamma)) \quad (9)$$

Here, $N_g$ is the number of filter lines that are assigned to the measured value to be filtered, the ray of which, starting from the radiation source position y(s), runs through the point x in the examination zone, and are used to determine the first filter value $P_g(s, x)$ for this measured value. Furthermore, $N_{ug}$ is the number of filter lines that are assigned to the measured value to be filtered, the ray of which, starting from the radiation position y(s), runs through the point x in the examination zone, and are used to determine the second filter value $P_{ug}(s, x)$ for this measured value. In addition, $\mu_{q,g}$ and $\mu_{q,ug}$ are filter factors, which are described in detail below. Furthermore, $\Theta_{q,g}(s, x, \gamma)$ is a unit vector, which, for a measured value to be filtered defined as described above by y(s) and x, indicates the qth filter line with corresponding filter direction, which is assigned to the measured value to be filtered and which is used to determine the first filter value for this measured value. Correspondingly, $\Theta_{q,ug}(s, x, \gamma)$ is a unit vector, which, for a measured value to be filtered defined as described above by y(s) and x, indicates the qth filter line with corresponding filter direction, which is assigned to the measured value to be filtered and which is used to determine the second filter value for this measured value. Finally, $\gamma$ is the κ-angle, which the direction vector $\Theta(s, x)=\Theta_{q,g}(s, x, 0)=\Theta_{q,ug}(s, x, 0)$ that runs, starting from the radiation source position y(s), through the point x in the examination zone, encloses with the unit vector $\Theta_{q,g}(s, x, \gamma)$ (when calculating a first mean value according to equation (8)) respectively $\Theta_{q,ug}(s, x, \gamma)$ (when calculating a second mean value according to equation (9)).

The relationship between the κ-angle $\gamma$, the qth filter line 71 for a measured value given by y(s) and x, and the unit vector $\Theta_q(s, x, \gamma)$ is illustrated by way of example in FIG. 6, the index "g" respectively "ug" having been omitted since this index is irrelevant for the illustration. If the qth filter line 71 of the measured value predetermined by the radiation source position y(s) and x is indicated at the location 73, then $\Theta_q(s, x, 0)$ denotes the ray that has caused the predetermined measured value at the location 73, and for different κ-angles γ≠0 the unit vector $\Theta_q(s, x, \gamma)$ samples the measured values on the qth filter line 71.

The filter lines and the associated filter directions for the measured values are now defined below:

Initially, a quantity of straight lines is defined as dividing lines $L_m$, wherein m can assume odd natural values of 1 to n in an nPi-acquisition. $L_1$ extends through the middle ($u_{P1}=0$, $v_{P1}=0$) of the planar detector 60 and asymptotically to the upper and lower Pi-boundary line. Furthermore, $L_1$ has a positive gradient based on the ($u_{P1}$, $v_{P1}$)-co-ordinate system 62. This is illustrated by way of example in FIG. 7, in which inter alia an upper Pi-boundary line 81, an upper 3Pi-boundary line 85, and upper 5Pi-boundary line 89, a lower Pi-boundary line 83, a lower 3Pi-boundary line 87 and a lower 5Pi-boundary line 91 of a 5Pi-acquisition can be seen. The line $L_1$ runs at the same time parallel to the derivative ẏ(s) at the respective current angular position s. For m>1, the lines $L_m$ extend parallel to $L_1$ and tangentially to the upper mPi-boundary line. In the case of the 5Pi-acquisition, in addition to the line $L_1$, the lines $L_3$ and $L_5$ are defined. Moreover, a quantity of dividing lines L-m is defined, which extend parallel to $L_1$ and tangentially to the lower mPi-boundary line. In the case of the 5Pi-acquisition, the lines $L_{-3}$ and $L_{-5}$ are defined. Furthermore, a dividing line $L_{-1}$ is defined that is the same as the dividing line $L_1$.

Furthermore, a quantity of dividing lines $L_{-p}{}^m$ is defined, which, in the above-mentioned orientation of the ($u_{P1}$, $v_{P1}$)-co-ordinate system 62 illustrated in FIGS. 7 to 14, have a negative gradient and extend both tangentially to the upper mPi-boundary line and tangentially to the lower pPi-boundary line, wherein p and m are odd, natural numbers less than or equal to n. Dividing lines $L_{-5}{}^1$, $L_{-3}{}^1$, $L_{-1}{}^1$, $L_{-1}{}^3$ and $L_{-1}{}^5$ are illustrated by way of example in FIG. 7.

Within the scope of the invention, the gradient of a line on the notional, planar detector surface relates to the ($u_{P1}$, $v_{P1}$)-co-ordinate system 62 used here and illustrated in FIGS. 7 to 14.

Furthermore, a quantity of dividing lines $L_p{}^m$ is defined, which, in the above-mentioned orientation of the ($u_{P1}$, $v_{P1}$)-co-ordinate system 62 illustrated in FIGS. 7 to 14, have a positive gradient and extend both tangentially to the upper mPi-boundary line and tangentially to the lower pPi-boundary line, wherein p and m are odd, natural numbers less than or equal to n. Dividing lines $L_3{}^7$, $L_3{}^5$, $L_5{}^5$, $L_5{}^3$ and $L_7{}^3$ are illustrated by way of example in FIG. 8.

In an nPi-acquisition, filter lines $F_l^{(R)}$, $G_u^{(R)}$ and $G_v^{(L)}$ are defined, wherein l assumes the values 1, 3, . . . , n,
u assumes the values 3, . . . , n−2, and
v assumes the values 1, 3, . . . , n−2.

The filter lines $F_l^{(R)}$ extend exclusively between the lPi-boundary lines, the filter lines $G_u^{(R)}$ extend exclusively between the uPi-boundary lines, and the filter lines $G_v^{(L)}$ extend exclusively between the vPi-boundary lines.

The filter direction 88 for filter lines $F_l^{(R)}$ and $G_u^{(R)}$ extends on the planar detector surface 60 in the orientation of the detector surface 60 illustrated in FIGS. 7 to 14 and of the ($u_{P1}$, $v_{P1}$)-co-ordinate system 62 substantially from left to right, that is, substantially in the direction of the $v_{P1}$-axis of the ($u_{P1}$, $v_{P1}$)-co-ordinate system 62. The filter direction 86 for filter lines $G_v^{(L)}$ extends on the planar detector surface 60 in the orientation of the detector surface 60 illustrated in FIGS. 7 to 14 and of the ($u_{P1}$, $v_{P1}$)-co-ordinate system 62 substantially from right to left, that is, substantially opposite to the direction of the $v_{P1}$-axis of the ($u_{P1}$, $v_{P1}$)-co-ordinate system. Several filter directions are indicated by arrows 86, 88 in FIGS. 9 to 14.

Each measured value to be filtered is assigned at least one of the filter lines $F_l^{(R)}$, $G_u^{(R)}$ and $G_v^{(L)}$, each of these assigned filter lines extending through the respective measured value.

The course of a filter line $F_l^{(R)}$ of a measured value to be filtered in conformity with (8) or (9) is defined so that the projection of the filter line $F_l^{(R)}$ that has been assigned to a measured value extends onto the planar detector surface (60) tangentially to the projection of the upper lPi-boundary line onto the planar detector surface (60), when the measured value lies on the planar detector surface (60) above a dividing line $L_l$. If this is not the case, then the filter line $F_l^{(R)}$ is so defined that the projection of the filter line $F_l^{(R)}$ that has been assigned to a measured value extends onto the planar detector surface (60) parallel to the projection of the dividing line $L_1$ onto the planar detector surface (60), when the measured values lies on the planar detector surface (60) above a dividing line $L_{-l}$. If this is also not the case, then the filter line $F_l^{(R)}$ is defined so that the projection of the filter line $F_l^{(R)}$ that has been assigned to a measured value extends onto the planar detector surface (60) tangentially to the projection of the lower lPi-boundary line onto the planar detector surface (60).

The projection of the filter line $F_l^{(R)}$ extends therefore inter alia tangentially to the projection of an upper or lower lPi-boundary line. In that case, it is additionally determined whether the particular filter line $F_l^{(R)}$ approaches the upper or lower lPi-boundary line on the notional, planar detector surface to the left or the right of the measured value to be filtered and to which the particular filter line $F_l^{(R)}$ is assigned, that is, whether the particular tangential point is located to the left or to the right of the measured value to be filtered.

To determine the position of a tangential point of a filter line $F_l^{(R)}$ extending tangentially to an upper lPi-boundary line, initially the tangential point of the dividing line $L_l$ is determined, that is, the point at which the dividing line $L_l$ contacts the upper lPi-boundary line. If the measured value to be filtered to which the filter line $F_l^{(R)}$ is assigned is arranged on the notional, planar detector to the left of this contact point, then the tangential point of the filter line $F_l^{(R)}$ is located to the right of the measured value to be filtered. If that is not the case, then the tangential point of the filter line $F_l^{(R)}$ is located to the left of the measured value to be filtered on the notional, planar detector surface.

To determine the position of a tangential point of a filter line $F_l^{(R)}$ extending tangentially to a lower lPi-boundary line, initially the tangential point of the dividing line $L_{-l}$ is determined, that is, the point at which the dividing line $L_{-l}$ contacts the lower lPi-boundary line. If the measured value to be filtered to which the filter line $F_l^{(R)}$ is assigned is arranged on the notional, planar detector to the left of this contact point, then the tangential point of the filter line $F_l^{(R)}$ is located to the right of the measured value to be filtered. If that is not the case, then the tangential point of the filter line $F_l^{(R)}$ is located to the left of the measured value to be filtered on the notional, planar detector surface.

The course of a filter line $G_u^{(R)}$ of a measured value to be filtered in conformity with equation (8) or (9) is defined by setting variables t and x to zero and carrying out the following steps α) to δ) until, for a filter line $G_u^{(R)}$ that is assigned to a measured value and for which the course is to be determined, a course has been determined, or until (u−t) is less than 3 or (3+x) is greater than u:

α) Checking whether the particular measured value on the planar detector surface 60 lies above the dividing line $L_{3+x}^{u-t}$. If this is the case, then the projection of the filter line $G_u^{(R)}$ that has been assigned to the measured value extends onto the planar detector surface (60) tangentially to the projection of the upper (u−t)Pi-boundary line onto the planar detector surface (60).

β) Adding the value two to the variable t.

γ) If the particular measured value does not lie above the dividing line $L_{3+x}^{u-t+2}$, (that is, if in step α) no course has been determined for the filter line $G_u^{(R)}$) and if (u−t) is greater than or equal to 3, then it is checked whether the particular measured value is located on the planar detector surface 60 above the dividing line $L_{3+x}^{u-t}$, taking into account the variable t increased by two. If this is the case, then the projection of the filter line $G_u^{(R)}$ that has been assigned to the measured value extends onto the planar detector surface (60) tangentially to the projection of the lower (3+x) Pi-boundary line onto the planar detector surface (60), δ) Adding the value two to the variable x.

If in steps α) to δ) it was not possible to determine a course for a filter line $G_u^{(R)}$ that is assigned to a measured value, that is to say, if determination of the course of the filter line $G_u^{(R)}$ by means of the steps α) to δ) has been terminated, since (u−t) has become less than 3 or (3+x) has become greater than u, then the filter line $G_u^{(R)}$ that is assigned to the particular measured value extends tangentially to the lower u Pi-boundary line.

For a filter line $G_u^{(R)}$, the particular tangential point is located to the left of the measured value to be filtered to which the particular filter line is assigned, when the filter line $G_u^{(R)}$ extends tangentially to a lower 3Pi-, 5Pi, . . . or uPi-boundary line. If, on the other hand, the filter line $G_u^{(R)}$ extends tangentially to an upper 3Pi-, 5Pi, . . . or uPi-boundary line, then the particular tangential point is located to the right of the measured value to be filtered.

The course of a filter line $G_v^{(L)}$ of a measured value to be filtered in conformity with equation (8) or (9) is defined by setting variables t and x to zero and carrying out the following steps ε) to θ) until, for a filter line $G_v^{(L)}$ that is assigned to a measured value and for which the course is to be determined, a course has been determined, or until (v−t) is less than 1 or (1+x) is greater than v:

ε) Checking whether the particular measured value lies on the planar detector surface 60 above the dividing line $L_{-(1+x)}^{v-t}$. If this is the case, then the projection of a filter line $G_v^{(L)}$ that has been assigned to a measured value extends onto the planar detector surface (60) tangentially to the projection of the lower (1+x)Pi-boundary line onto the planar detector surface (60).

ζ) Adding the value two to the variable t.

η) If the particular measured value does not lie above the dividing line $L_{-(1+x)}^{v-t+2}$, (that is, if in step α) no course has been determined for the filter line $G_u^{(R)}$) and if (v−t) is greater than or equal to 1, then it is checked whether the particular measured value lies on the planar detector surface 60 above the dividing line $L_{-(1+x)}^{v-t}$, taking into account the variable t increased by the value two. If this is the case, then the projection of the filter line $G_v^{(L)}$ that has been assigned to the measured value extends onto the planar detector surface (60) tangentially to the projection of the lower (1+x)Pi-boundary line onto the planar detector surface (60).

θ) Adding the value two to the variable x.

If in steps ε) to θ) it was not possible to determine a course for a filter line $G_v^{(L)}$ that is assigned to a measured value, that is to say, if determination of the course of the filter line $G_v^{(L)}$ by means of the steps ε) to θ) has been terminated, since (v−t) has become less than 1 or (1+x) has become greater than u, then the filter line $G_v^{(L)}$ that is assigned to the particular measured value extends tangentially to the lower vPi-boundary line.

For a filter line $G_v^{(L)}$, the particular tangential point is located to the left of the measured value to be filtered to which the particular filter line is assigned, when the filter line $G_v^{(L)}$ extends tangentially to an upper Pi-, 5Pi, . . . or vPi-boundary line. If, on the other hand, the filter line $G_v^{(L)}$ extends tangentially to a lower Pi-, 5Pi, . . . or vPi-boundary line, then the particular tangential point is located to the right of the measured value to be filtered.

Figure 9:
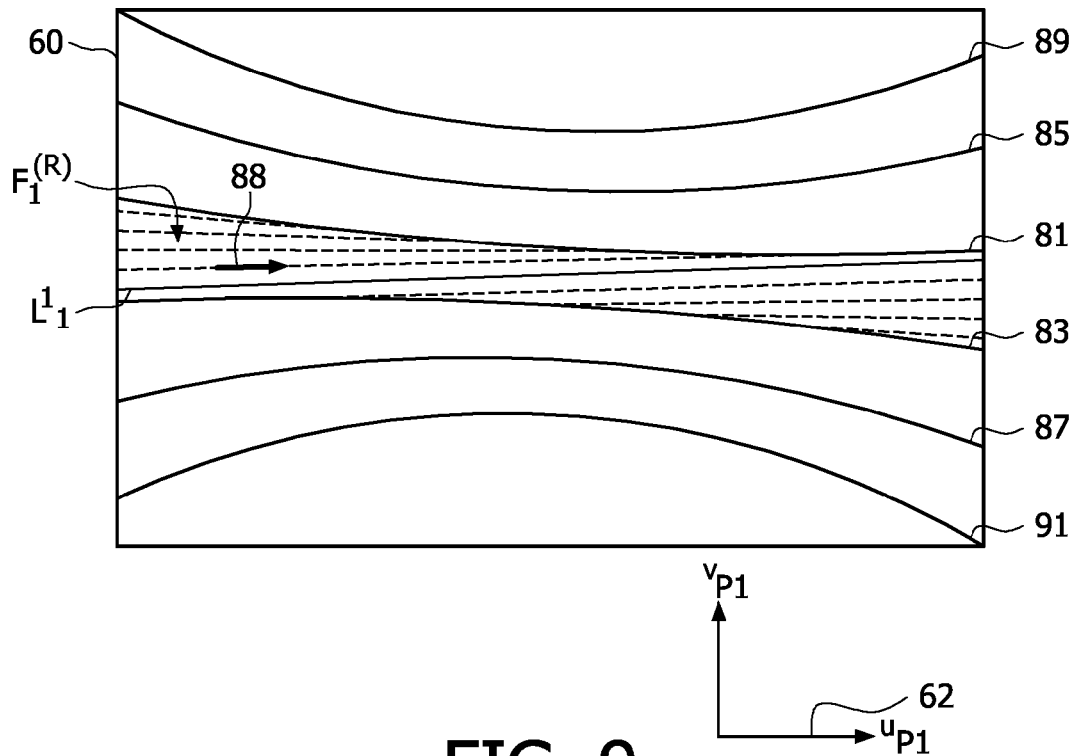
Figure 10:
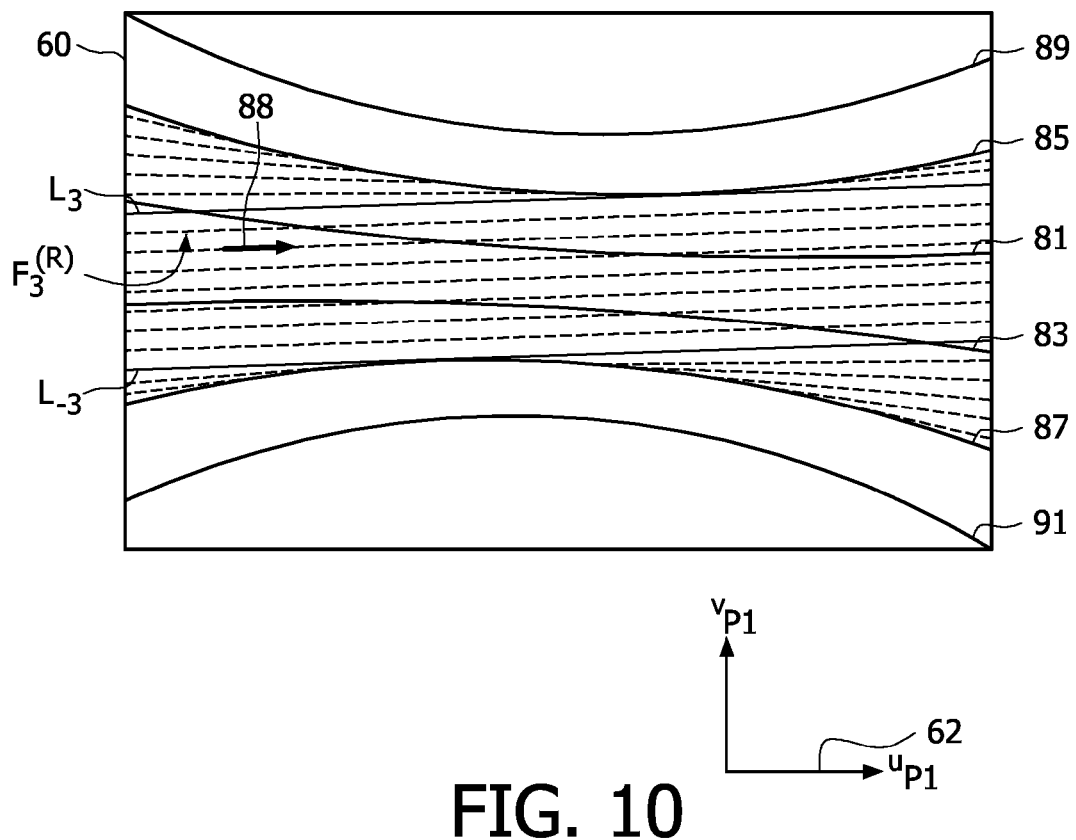
Figure 11:
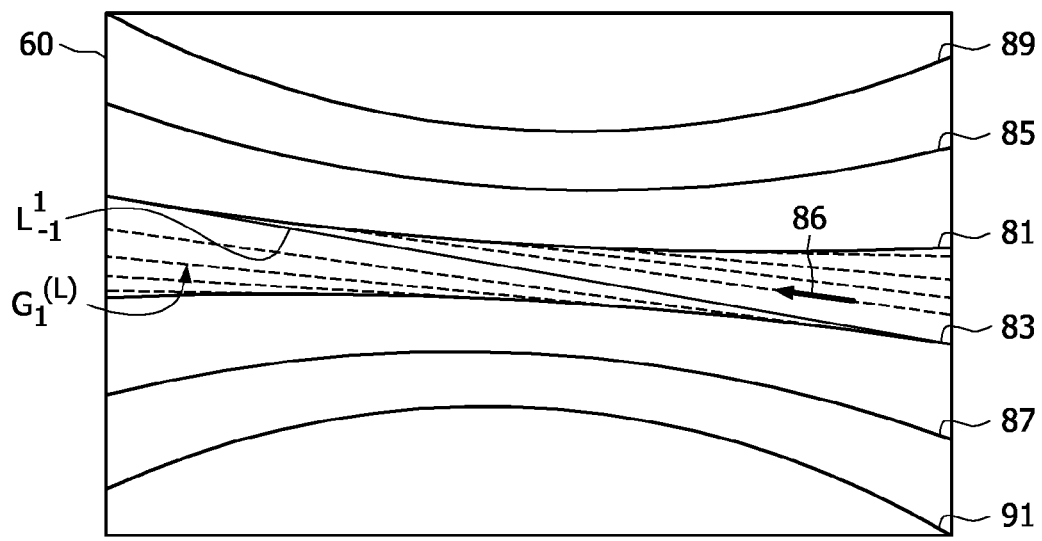
Figure 12:
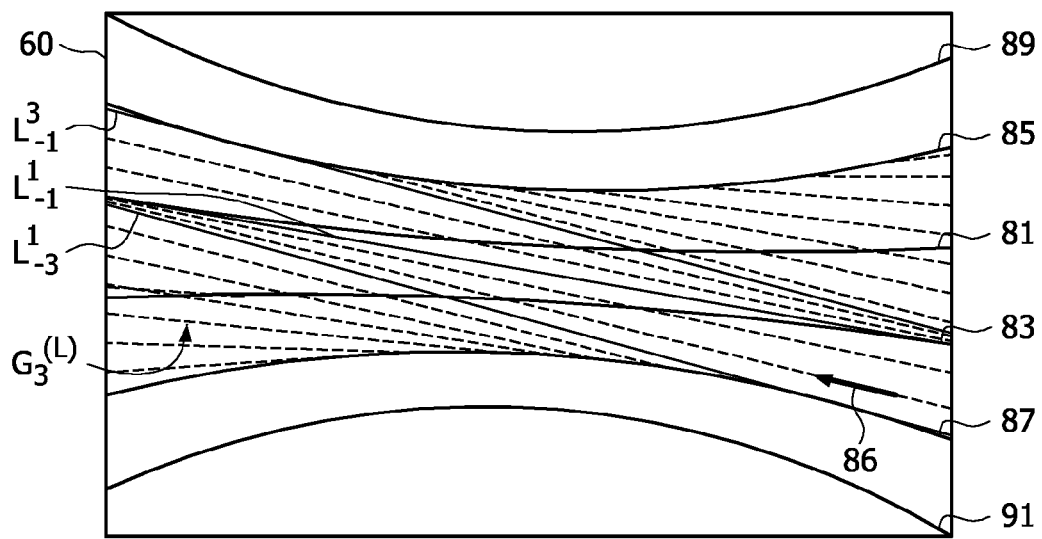

The course of several filter lines is illustrated as an example in FIGS. 9 to 14, the filter lines in these Figures each being shown by a broken line. In FIG. 9, several filter lines $F_1^{(R)}$ are shown and in FIG. 10 several filter lines $F_3^{(R)}$ are shown, in each case during a 5Pi-relative movement. In FIG. 11, several filter lines $G_1^{(L)}$ are shown and in FIG. 12 several filter lines $G_3^{(L)}$ are shown, likewise during a 5Pi-relative movement. In FIG. 13, several filter lines $G_3^{(R)}$ are shown and in FIG. 14 several filter lines $G_5^{(R)}$ are shown, in each case during a 7Pi-relative movement, the upper 7Pi-line bearing the reference numeral 90 and the lower 7Pi-line bearing the reference numeral 93.

The number of filter lines that is assigned to a measured value therefore depends on its position on the detector surface and on the selected "n" in the nPi-relative movement.

If the measured value lies between two Pi-boundary lines, then the filter lines $F_1^{(R)}, F_3^{(R)}, \ldots, F_n^{(R)}, G_3^{(R)}, G_5^{(R)}, \ldots, G_{n-2}^{(R)}, G_1^{(L)}, G_3^{(L)}, \ldots, G_{n-2}^{(L)}$ are assigned to the measured value. If the particular measured value lies between two rPi-boundary lines, but not between two (r−2)Pi-boundary lines, wherein r is greater than 1 and less than n, then the filter lines $F_r^{(R)}, F_{r+2}^{(R)}, \ldots, F_n^{(R)}, G_r^{(L)}, G_{r+2}^{(L)}, \ldots, G_{n-2}^{(L)}, G_r^{(R)}, G_{r+2}^{(R)}, \ldots, G_{n-2}^{(R)}$ are assigned to the measured value. If the particular measured value is between two nPi-boundary lines, but not between two (n−2)Pi-boundary lines, then the filter line $F_n^{(R)}$ is assigned to the measured value.

For example, during a 5Pi-relative movement, the filter lines $F_1^{(R)}, F_3^{(R)}, F_5^{(R)}, G_3^{(R)}, G_1^{(L)}$ and $G_3^{(L)}$ are assigned to a measured value that lies between the Pi-boundary lines. The filter lines $F_3^{(R)}, F_5^{(R)}, G_3^{(R)}$ and $G_3^{(L)}$ are assigned to a measured value that lies between the 3Pi-boundary lines but not between the Pi-boundary lines. Finally, the filter line $F_5^{(R)}$ is assigned to a measured value that lies between the 5i-boundary lines but not between the 3Pi-boundary lines.

The filter lines $F_1^{(R)}, G_u^{(R)}$ and $G_v^{(L)}$ are for a specific location, that is, for a specific position of the measured value on the detector surface exclusively dependent on the acquisition geometry used, that is, on the dimensions of the computer tomograph and on the pitch selected. In known acquisition geometry, the filter lines $F_i^{(R)}, G_u^{(R)}$ and $G_v^{(L)}$ can thus be determined immediately and not first in step 105.

Next, the measured values projected onto the planar detector 60 are filtered in step 106 along the filter lines and filter directions predetermined in step 105 in conformity with equation (8) and (9), so that per measured value and associated filter line a respective intermediate filter value is determined.

For that purpose, first of all a measured value to be filtered and a filter line assigned to this measured value are selected.

Along this filter line, measured values that lie on the filter line are each multiplied in the filter direction with a κ-factor and added. The κ-factor decreases here as the sine of the κ-angle increases. The κ-factor is in particular equal to the reciprocal of the sine of the κ-angle. The result of the summation is an intermediate filter value. This is repeated for all filter lines of the measured value to be filtered, so that for this measured value and for each filter line assigned to this measured value a respective intermediate filter value is determined, that is, an intermediate filter value is assigned to each filter line that is assigned to a measured value.

The reciprocal of the sine of the κ-angle is known as κ-filter, wherein a function that corresponds to the reciprocal of the sine of the κ-angle, but does not represent it exactly, is also known as κ-filter. For example, the Taylor development of said reciprocal is also known as κ-filter.

To determine an intermediate filter value for a measured value to be filtered and a filter line assigned to this measured value, those measured values that lie on this filter line are preferably interpolated on the planar detector 60 in such a way that they are arranged on this filter line equidistantly with respect to the κ-angle. The interpolated measured values are then multiplied by the κ-factor according to equation (8) or (9) along the filter line and added to form an intermediate filter value, wherein multiplication by the κ-factor and the summation can be carried out in known manner by means of a Fourier transform.

Filtering was here carried out on the planar detector. Alternatively, it can be carried out on any desired detector. The measured values and the filter lines would then have to be projected onto this detector. In particular it can be sensible to filter the measured values on the focus-centered detector, so that the projection of the measured values onto the planar detector carried out in step 104 can be omitted.

In step 107, first and second filter values are determined from the intermediate filter values. For that purpose, the intermediate filter values of a measured value, as far as they are assigned to the filter lines $F_{n-2}^{(R)}$, $F_n^{(R)}$, $G_{n-2}^{(R)}$ and $G_{n-2}^{(L)}$ are combined linearly to form a first filter value $P_g$ for this measured value (this corresponds to the multiplication by the factors $\mu_{q,g}$ and the summation in equation (8)). Furthermore, the intermediate filter values of a measured value, so far as they are assigned to the filter lines $F_1^{(R)}$, $F_3^{(R)}$, ..., $F_{n-2}^{(R)}$, $G_1^{(L)}$, $G_3^{(L)}$, ..., $G_{n-2}^{(L)}$, $G_3^{(R)}$, $G_5^{(R)}$, ..., $G_{n-2}^{(R)}$, are combined linearly to form a second filter value $P_{ug}$ for this measured value (this corresponds to the multiplication by the factors $\mu_{q,ug}$ and the summation in equation (9)).

In determining the first filter value $P_g$ by means of a linear combination, the intermediate filter values that are assigned to the filter lines $F_{n-2}^{(R)}$, $F_n^{(R)}$, $G_{n-2}^{(R)}$ and $G_{n-2}^{(L)}$, are multiplied by the following filter factors $\mu_{q,g}$:

an intermediate filter value, which is assigned to a filter line $F_{n-2}^{(R)}$, is multiplied by the filter factor −1, an intermediate filter value, which is assigned to a filter line $F_n^{(R)}$, is multiplied by the filter factor 1, an intermediate filter value, which is assigned to a filter line $G_{n-2}^{(R)}$, is multiplied by the filter factor ½, an intermediate filter value, which is assigned to a filter line $G_{n-2}^{(L)}$ is multiplied by the filter factor −½.

In determining the second filter value $P_{ug}$ by means of a linear combination, the intermediate filter values that are assigned to the filter lines $F_1^{(R)}$, $F_3^{(R)}$, ..., $F_{n-2}^{(R)}$, $G_1^{(R)}$, $G_3^{(L)}$, ..., $G_{n-2}^{(L)}$, $G_3^{(R)}$, $G_5^{(R)}$, ..., $G_{n-2}^{(R)}$, are multiplied by the following filter factors $\mu_{q,ug}$:

an intermediate filter value, which is assigned to a filter line $F_1^{(R)}$, is multiplied by the filter factor n/3, an intermediate filter value, which is assigned to a filter line $F_{n-2}^{(R)}$, is multiplied by the filter factor n/(n−2), an intermediate filter value, which is assigned to a filter line $F_k^{(R)}$, with 1<k<n−2, is multiplied by the filter factor 2n/(k(k+2)), an intermediate filter value, which is assigned to a filter line $G_{n-2}^{(R)}$, is multiplied by the filter factor n/(2(n−2)), an intermediate filter value, which is assigned to a filter line $G_z^{(R)}$, with z<n−2, is multiplied by the filter factor −n/(z(z+2)), an intermediate filter value, which is assigned to a filter line $G_{n-2}^{(L)}$, is multiplied by the filter factor n/(2(n−2)), an intermediate filter value, which is assigned to a filter line $G_d^{(L)}$, with d<n−2, is multiplied by the filter factor n/(d(d+2)).

In order to determine a first filter value $P_g$ for a measured value, it is first checked which of the filter lines $F_{n-2}^{(R)}$, $F_n^{(R)}$, $G_{n-2}^{(R)}$ and $G_{n-2}^{(L)}$ have been assigned to the measured value. For each of these assigned filter lines a respective intermediate filter value is determined. Each intermediate filter value determined is multiplied by the corresponding above-mentioned filter factor, and the intermediate filter values multiplied by the respective filter factor are added to form a first filter value $P_g$.

Correspondingly, in order to determine a second filter value $P_{ug}$ for a measured value, it is first checked which of the filter lines $F_1^{(R)}$, $F_3^{(R)}$, ..., $F_{n-2}^{(R)}$, $G_1^{(L)}$, $G_3^{(L)}$, ..., $G_{n-2}^{(L)}$, $G_3^{(R)}$, $G_5^{(R)}$, ..., $G_{n-2}^{(R)}$ have been assigned to the measured value. For each of these assigned filter lines a respective intermediate filter value is determined. Each intermediate filter value determined is multiplied by the corresponding above-mentioned filter factor, and the intermediate filter values multiplied by the respective filter factor are added to form a second filter value $P_{ug}$.

This method is repeated for each measured value that during the nPi-relative movement is located between the nPi-boundary lines, so that for each of these measured values, when the corresponding filter lines have been assigned to it, a first and/or a second filter value is determined.

The first filter values form a first group, and the second filter values form a second group.

In step 108, the first filter values $P_g$, that is, the filter values of the first group, are weighted in dependence on the movement of the object.

Each first filter value has been determined from measured values that have been acquired at the same instant, that is, each first filter values can be assigned an instant and hence, when considering the electrocardiogram, a cardiac movement phase. For weighting the first filter values, weighting methods known, for example, from cardiac imaging can therefore be used, the sole difference being that, in place of the measured values, the first filter values are weighted in dependence on the movement of the object. These weighting methods are known to those skilled in the art, for example, from "Adaptive temporal resolution in medical cardiac cone beam CT reconstruction", R. Manzke, M. Grass, T. Nielsen, G. Shechter, D. Hawkes, Medical Physics, Vol. 30, No. 12, pages 3072 to 3080, December 2003, so that only brief details of the weighting of the first filter values are given.

The periodic movement of the object to be examined is known on the basis of the electrocardiogram recorded during acquisition of the measured values. In other embodiments, the movement of the object could, as stated above, be determined in a different manner. It is thus known in which time ranges within a movement period the object has moved more slowly and in which time ranges the object has moved more quickly, that is, in which time ranges the object has moved more quickly than in other time ranges. Relative to the period duration a base instant is therefore defined, which preferably lies centrally in a time range within a period in which the object has moved relatively little.

As a rule, the time ranges within a period in which the object is moving relatively little are known, so that the base instant relative to the movement period can be determined in advance. For example, in the case of the human heart it is known that it moves relatively little in a time range that is arranged around 70%-RR, meaning, when a base instant lies at 70%-RR, that at the base instant 70% of the particular time range, that is, the interval between two adjacent R-peaks, is deleted.

Base instants that lie in time ranges in which the object is moving as little as possible, can also, for example, be determined by the method described in "Automatic phase-determination for retrospectively gated cardiac CT", R. Manzke, Th. Köhler, T. Nielsen, D. Hawkes, M. Grass, Medical Physics, Vol. 31, No. 12, pages 3345 to 3362, December 2004.

When the object is a heart, then the base instant preferably lies in the diastolic phase and not in the systolic phase, since in the diastolic phase the heart moves less than in the systolic phase.

Around each base instant there is a time range of predetermined length, the base instant forming the middle of the respective time range. The length of the time ranges depends on how many measured values from which angular ranges are required for the reconstruction. The length of the time ranges is therefore to be chosen so that, after weighting, the quantity of measured values necessary for the applied reconstruction method is available.

In this embodiment, time ranges are determined for each voxel, wherein the time range for the respective voxel is so large that for the respective voxel, after weighting in dependence on the movement of the object, the Pi-criterion in respect of the weighted first filter values is fulfilled. The Pi-criterion is explained in detail below.

Once the base instants have been determined and time ranges have been arranged around the base instants, first filter values that have been determined from measured values that have been acquired within these time ranges are multiplied by 1. The remaining first filter values are multiplied by 0, that is, are ignored in the back-projection described below.

It can be checked whether the Pi-criterion for a voxel in respect of the weighted first filter values is fulfilled as follows: First of all a plane that is oriented perpendicularly to the axis of rotation and runs through this voxel is defined. Then, those regions of the helix which, during the measurement, issue rays that run through this voxel and whose associated measured values have been acquired at instants that lie within the time ranges around the base instants, are projected onto this plane in the direction of the axis of rotation. When these helix segments projected onto the plane form a segment of circle, which is bounded by a straight line that runs through this voxel, then the Pi-criterion for that voxel is fulfilled.

As already mentioned above, this weighting in dependence on the movement of the object represents just one example. Other known methods, for example, methods in which the first filter values are weighted in dependence on their distance from the base instant, can also be used to weight the first filter values in dependence on the movement of the object.

In step 109, the weighted first filter values and the second filter values for reconstruction of the absorption distribution in the examination zone are back-projected substantially in conformity with the following equation, only measured values and filter values that lie between the two nPi-lines being taken into account:

$$f_{g,ug}(x) = \frac{(-1)1}{2\pi^2} \frac{1}{n} \int \frac{ds}{|x-y(s)|} P_{g,ug}(s,x). \tag{10}$$

Here, $f_g(x)$ is the value of the CT image at the location x in the examination zone, which is obtained by back-projection of the weighted first filter values. Furthermore, $f_{ug}(x)$ is the value of the CT image at the location x in the examination zone that is obtained by back-projection of the second filter values.

First of all the weighted first filter values are back-projected.

The back-projection is explained below with reference to the flow chart illustrated in FIG. 15. Alternatively, other known back-projection methods can be used.

In step 201, a location x and a voxel V(x) arranged at this location are predetermined within a predeterminable field of view (FOV) in the examination zone, wherein a voxel V(x) that has not yet been reconstructed in the preceding back-projection steps is selected.

Then, in step 203, the quantity of angular positions s or radiation source positions y(s) giving off rays that pass centrally through the voxel V(x) and are incident on the detector surface between the nPi-boundary lines is determined.

Then, in step 205, an angular position s that has not yet been used for reconstruction of the voxel V(x) is predetermined from the quantity of angular positions determined in step 203.

In step 207, a weighted first filter value is determined for the ray starting from the radiation source position y(s) determined by the predetermined angular position s and passing centrally through the voxel (x). If the detector surface, as in this embodiment, is made up of several rectangular detector elements, each of which records a measured value, then, when the ray is incident centrally on a detector element, the weighted first filter value that is assigned to this measured value recorded by this detector pixel is determined for this ray. If this ray is not incident centrally on a detector element, then a weighted first filter value is determined by interpolation from the weighted first filter value that is assigned to the measured value recorded by the detector element on which the ray is incident, and from adjacent weighted first filter values, for example, by a bilinear interpolation. If, however, as described above, the first filter values are multiplied by one or zero, then in step 207 a weighted first filter value is, of course, determined only when the radiation source has assumed the angular position predetermined in step 205 at an instant that lies in one of the time ranges arranged around the base instant. If this is not the case, then the sequence can be continued directly with step 213.

The weighted first filter value determined in step 207 is multiplied in step 209 by a further weighting factor that decreases as the distance of the radiation source y(s) from the location x predetermined in step 201 increases. In this embodiment, in conformity with equation (10) this weighting factor is equal to $1/|x-y(s)|$.

In step 211, the weighted filter value on the voxel V(x), which is preferably initially the same, is added.

In step 213, it is checked whether all angular positions s from the quantity of angular positions determined in step 203 have been taken into account in the reconstruction of the voxel V(x). If this is not the case, then the flowchart branches to step 205. Otherwise in step 215 it is checked whether all voxels V(x) have been reconstructed in the FOV. If this is not the case, then the sequence is continued with step 201. If, on the other hand, all voxels V(x) in the FOV have passed through, then the absorption in the entire FOV, and hence a CT image, has been determined, and the back-projection of the weighted first filter values is terminated.

The second filter values are correspondingly back-projected, that is, the second filter values, as described above in connection with the steps 201 to 215, are back-projected (in the above description essentially in each case the weighted first filter value is to be replaced by the second filter value).

The CT images that have been determined by back-projection of the weighted first filter values and the second filter values are added voxel-wise, the CT image resulting from the summation being the definitively reconstructed CT image of the examination zone, whereby the computed tomography method according to the invention is ended (step 110).

Alternatively, the weighted first filter values and the second filter values can be combined before back-projection, that is, for example, can be combined linearly or added, wherein then only the combined filter values are to be back-projected to the final CT image.

The invention claimed is:

1. A computed tomography method having the following steps:
   a) generation with a radiation source of a conical beam bundle passing through an examination zone and a periodically moving object located therein,
   b) generation of a nPi-relative movement between the radiation source on the one hand and the examination zone on the other hand, which comprises a rotation about an axis of rotation and a displacement in a displacement direction parallel to the axis of rotation and takes the form of a helix,
   c) acquisition by means of the detector unit, during the nPi-relative movement, of measured values that are dependent on the intensity in the beam bundle on the other side of the examination zone,
   d) determination of filter values by filtering the measured values and dividing the filter values into different groups,
   e) weighting of the filter values of at least one group in dependence on the movement of the object, wherein, when filter values of several groups are weighted, filter values of different groups are differently weighted in dependence on the movement of the object,
   f) reconstruction of a CT image of the examination zone from the filter values.

2. A computed tomography method as claimed in claim 1, wherein in step f) the reconstruction is carried out by back-projecting the filter values into the examination zone.

3. A computed tomography method as claimed in claim 1, wherein in step d) the measured values are filtered with a κ-filter.

4. A computed tomography method as claimed in claim 1, wherein, before the filtering in step d), the measured values are derived, wherein each measured value is assigned a ray and wherein in each case measured values whose associated rays run parallel are derived partially in accordance with the angular position of the radiation source on the helix, from which radiation source the particular parallel rays issue.

5. A computed tomography method as claimed in claim 1, wherein, in step d), the filter values are filtered by filtering the measured values in such a manner and are divided into groups in such a manner that filter values of different groups comprise contributions of radon planes that intersect the helix with varying frequency.

6. A computed tomography method as claimed in claim 5, wherein filter values of a group are weighted more heavily in dependence on the movement of the object the more frequently the radon planes whose contributions are contained by the filter values of the particular group intersect the helix.

7. A computed tomography method as claimed in claim 1, wherein, in step d), first and second filter values are determined by filtering the measured values in such a manner that the first filter values comprise contributions of radon planes that intersect the helix at least n times, and the second filter values comprise contributions of radon planes that intersect the helix fewer than n times,
   in that the filter values in step d) are divided into different groups in such a manner that the first filter values form a first group and the second filter values form a second group, and
   in that, in step e), the filter values of the first group are weighted more heavily in dependence on the movement of the object than the filter values of the second group.

8. A computed tomography method as claimed in claim 7, wherein, in step d), for each measured value the first and/or second filter values are determined according to the following steps:
   assignment of at least one filter line to the particular measured value, wherein, when the particular measured value lies between two Pi-boundary lines, the filter lines $F_l^{(R)}$, $G_u^{(R)}$ and $G_v^{(L)}$ are assigned to the particular measured value, wherein
   l assumes the values $1, 3, \ldots, n$,
   u assumes the values $3, \ldots, n-2$, and
   v assumes the values $1, 3, \ldots, n-2$,
   wherein, when the particular measured value lies between two rPi-boundary lines, but not between two (r−2)Pi-boundary lines, wherein r is greater than 1 and less than n, the filter lines $F_r^{(R)}, F_{r+2}^{(R)}, \ldots, F_n^{(R)}, G_r^{(L)}, G_{r+2}^{(L)}, \ldots, G_{n-2}^{(L)}, G_r^{(R)}, G_{r+2}^{(R)}, \ldots, G_{n-2}^{(R)}$ are assigned to the particular measured value,
   wherein, when the particular measured value lies between two nPi-boundary lines, but not between two (n−2)Pi-boundary lines, the filter line $F_n^{(R)}$ is assigned to the particular measured value,
   determining in each case an intermediate filter value for each filter line that is assigned to the particular measured value, by filtering the measured values that lie on the particular filter line and adding the filtered measured values lying on the particular filter line to form an intermediate filter value, so that for each filter line assigned to the particular measured value an intermediate filter value is determined, which is assigned to the particular measured value and the particular filter line,
   forming a first filter value by linear combination of those intermediate filter values of the particular measured value that are assigned to the filter lines $F_{n-2}^{(R)}$, $F_n^{(R)}$, $G_{n-2}^{(R)}$ and $G_{n-2}^{(L)}$, and forming a second filter value by linear combination of those intermediate filter values of the particular measured value that are assigned to the filter lines $F_1^{(R)}, F_3^{(R)}, \ldots, F_{n-2}^{(R)}, G_1^{(L)}, G_3^{(L)}, \ldots, G_{n-2}^{(L)}, G_3^{(R)}, G_5^{(R)}, \ldots, G_{n-2}^{(R)}$,
   wherein to determine the course of the associated at least one filter line $F_1^{(R)}$, $G_u^{(R)}$ and $G_v^{(L)}$, first of all dividing lines $L_m, L_{-m}, L_p^m$ and $L_{-p}^m$ with $m=1, 3, \ldots, n$ and $p=1, 3, \ldots, n$ are determined, the projections of which onto a notional, planar detector surface that contains the axis of rotation and the surface normal of which runs through the respective radiation source position y(s) extend as follows:
   the projection of the dividing line $L_1$ is parallel to the projection of the derivative ẏ(s) of the radiation source position y(s) onto the planar detector surface, the projection of the dividing line $L_{-1}$ is the same as the projection of the dividing line $L_1$, the projection of the dividing line $L_m$ for m>1 is parallel to the projection of $L_1$ and tangential to the projection of the upper mPi-boundary line onto the planar detector surface, the projection of the dividing line $L_{-m}$ for m>1 is parallel to the projection of $L_1$ and tangential to the projection of the lower mPi-boundary line onto the planar detector surface, the projection of the dividing line $L_{-p}{}^m$ is tangential to the projection of the upper mPi-boundary line onto the planar detector surface and tangential to the projection of the lower pPi-boundary line onto the planar detector surface and has a negative gradient with respect the planar detector surface, the projection of the dividing line $L_p{}^m$ is tangential to the projection of the upper mPi-boundary line onto the planar detector surface and tangential to the projection of the lower pPi-boundary line onto the planar detector surface and has a positive gradient with respect to the planar detector surface, wherein the filter lines $F_l^{(R)}, G_u^{(R)}$ and $G_v^{(L)}$ that are assigned to the particular measured value extend through the particular measured value, wherein the filter line $F_l^{(R)}$ extends exclusively between the lPi-boundary lines, wherein the filter line $G_u^{(R)}$ extends exclusively between the uPi-boundary lines, wherein the filter line $G_v^{(L)}$ extends exclusively between the vPi-boundary lines and i) wherein the projection of a filter line $F_l^{(R)}$ that has been assigned to a measured value extends onto the planar detector surface tangentially to the projection of the upper lPi-boundary line onto the planar detector surface, when the measured value lies above a dividing line $L_l$, ii) wherein the projection of a filter line $F_l^{(R)}$ that has been assigned to a measured value extends onto the planar detector surface parallel to the projection of the dividing line $L_1$ onto detector surface, when i) does not apply and the measured value lies on the planar detector surface above a dividing line $L_{-l}$, iii) wherein the projection of a filter line $F_l^{(R)}$ that has been assigned to a measured value extends onto the planar detector surface tangentially to the projection of the lower lPi-boundary line onto the planar detector surface, when i) and ii) do not apply, iv) wherein the course of a filter line $G_u^{(R)}$ that has been assigned to a measured value is determined by setting variables t and x to zero and carrying out the following steps α) to δ) until, for a filter line $G_u^{(R)}$ that is assigned to a measured value and for which the course is to be determined, a course has been determined, or until (u–t) is less than 3 or (3+x) is greater than u:

α) checking whether the particular measured value lies on the planar detector surface above the dividing line $L_{3+x}{}^{u-t}$, wherein, if this is the case, the projection of the filter line $G_u^{(R)}$ that has been assigned to the measured value extends onto the planar detector surface tangentially to the projection of the upper (u–t)Pi-boundary line onto the planar detector surface, β) adding the number two to the variable t, γ) if the particular measured value does not lie above the dividing line $L_{3+x}{}^{u-t+2}$, that is, if in step α) no course has been determined for the filter line $G_u^{(R)}$, and if (u–t) is greater than or equal to 3, checking whether the particular measured value lies on the planar detector surface above the dividing line $L_{3+x}{}^{u-t}$ taking into account the variable t increased by two, wherein, if this is the case, the projection of the filter line $G_u^{(R)}$ that has been assigned to the measured value extends onto the planar detector surface tangentially to the projection of the lower (3+x)Pi-boundary line onto the planar detector surface, δ) adding the number two to the variable x, v) wherein, if in steps α) to δ) for a filter line $G_u^{(R)}$ that is assigned to a measured value no course of the filter line $G_u^{(R)}$ has been determined, the filter line $G_u^{(R)}$ extends tangentially to the lower uPi-boundary vi) wherein the course of a filter line $G_v^{(L)}$ that has been assigned to a measured value is determined by setting variables t and x to zero and carrying out the following steps ε) to θ) until, for a filter line $G_v^{(L)}$ that is assigned to a measured value and for which the course is to be determined, a course has been determined, or until (v–t) is less than 1 or (1+x) is greater than v:

ε) checking whether the particular measured value lies on the planar detector surface above the dividing line $L_{-(1+x)}{}^{v-t}$, wherein, if this is the case, then the projection of the filter line $G_v^{(L)}$ that has been assigned to the measured value extends onto the planar detector surface tangentially to the projection of the upper (v–t) Pi-boundary line onto the planar detector surface, ζ) adding the number two to the variable t, η) if the particular measured value does not lie above the dividing line $L_{-(1+x)}{}^{v-t+2}$, that is, if in step c) no course has been determined for the filter line $G_v^{(L)}$s, and if (v–t) is greater than or equal to 1, checking whether the particular measured value lies on the planar detector surface above the dividing line $L_{-(1+x)}{}^{v-t}$ taking into account the variable t increased by two, wherein, if this is the case, the projection of the filter line $G_v^{(L)}$ that has been assigned to the measured value extends onto the planar detector surface tangentially to the projection of the lower (1+x)Pi-boundary line onto the planar detector surface, θ) adding the number two to the variable x, vii) wherein, if in steps ε) to θ) for a filter line $G_v^{(L)}$ that is assigned to a measured value, no course of the filter line $G_v^{(L)}$ has been determined, the filter line $G_v^{(L)}$ extends tangentially to the lower vPi-boundary line.

9. A computed tomography method as claimed in claim 8, wherein a filter direction is assigned to each filter line, wherein the filter directions that are assigned to the filter lines $F_l^{(R)}$ and $G_u^{(R)}$, projected onto the planar detector surface (60), point substantially from left to right, and the filter directions that are assigned to the filter lines $G_v^{(L)}$, projected onto the planar detector surface, point substantially from right to left.

10. A computed tomography method as claimed in claim 8, wherein when the projection of a filter line $G_v^{(L)}$ onto the planar detector surface extends tangentially to the projection of one of the upper sPi-boundary lines with s=1, 3, . . . , v, the projection of the filter line $G_v^{(L)}$ approaches one of the upper sPi-boundary lines in a region of the projection that is located to the left of the projection onto the planar detector surface of the measured value to be filtered, in that when the projection of a filter line $G_v^{(L)}$ onto the planar detector surface extends tangentially to the projection of one of the lower sPi-boundary lines with s=1, 3, . . . , v, the projection of the filter line $G_v^{(L)}$ approaches one of the lower sPi-boundary lines in a region of the projection that is located to the right of the projection onto the planar detector surface of the measured value to be filtered, in that when a projection of the filter line $G_u^{(R)}$ onto the planar detector surface extends tangentially to the projection of one of the upper pPi-boundary lines with p=3, ..., u onto the detector surface, the projection of the filter line $G_u^{(R)}$ approaches the upper pPi-boundary line in a region that is located to the right of the projection onto the planar detector surface of the measured value to be filtered, in that when the projection of a filter line $G_u^{(R)}$ onto the planar detector surface extends tangentially to the projection of one of the lower pPi-boundary lines with p=3, ..., u, the projection of the filter line $G_u^{(R)}$ approaches one of the lower pPi-boundary lines in a region of the projection that is located to the left of the projection onto the planar detector surface of the measured value to be filtered, in that when the projection of a filter line $F_l^{(R)}$ onto the planar detector surface extends tangentially to the projection of the upper lPi-boundary line onto the planar detector surface and when the location at which the projection of the dividing line $L_l$ onto the planar detector surface tangentially contacts the projection of the upper lPi-boundary line is located to the left of the projection onto the planar detector surface of the measured value to be filtered, the projection of the filter line $F_l^{(R)}$ approaches the upper lPi-boundary line in a region of the projection that is located to the left of the projection onto the planar detector surface of the measured value to be filtered, in that when the projection of a filter line $F_l^{(R)}$ onto the planar detector surface extends tangentially to the projection of the upper lPi-boundary line onto the planar detector surface and when the location at which the projection of the dividing line $L_l$ onto the planar detector surface tangentially contacts the projection of the upper lPi-boundary line is located to the right of the projection onto the planar detector surface of the measured value to be filtered, the projection of the filter line $F_l^{(R)}$ approaches the upper lPi-boundary line in a region of the projection that is located to the right of the projection onto the planar detector surface of the measured value to be filtered, in that when the projection of a filter line $F_l^{(R)}$ onto the planar detector surface extends tangentially to the projection of the lower lPi-boundary line onto the planar detector surface and when the location at which the projection of the dividing line onto the planar detector surface tangentially contacts the projection of the lower lPi-boundary line is located to the left of the projection onto the planar detector surface of the measured value to be filtered, the projection of the filter line $F_l^{(R)}$ approaches the lower lPi-boundary line in a region of the projection that is located to the left of the projection onto the planar detector surface of the measured value to be filtered, in that when the projection of a filter line $F_l^{(R)}$ onto the planar detector surface extends tangentially to the projection of the lower lPi-boundary line onto the planar detector surface and when the location at which the projection of the dividing line $L_{-l}$ onto the planar detector surface tangentially contacts the projection of the lower lPi-boundary line is located to the right of the projection onto the planar detector surface of the measured value to be filtered, the projection of the filter line $F_l^{(R)}$ approaches the lower lPi-boundary line in a region of the projection that is located to the right of the projection onto the planar detector surface of the measured value to be filtered.

11. Computed tomography method as claimed in claim 8, wherein on forming a first filter value by linear combination of those intermediate filter values of the particular measured value which are assigned to the filter lines $F_{n-2}^{(R)}$, $F_n^{(R)}$, $G_{n-2}^{(R)}$ and $G_{n-2}^{(L)}$, an intermediate filter value, which is assigned to a filter line $F_{n-2}^{(R)}$, is multiplied by the factor $-1$, an intermediate filter value, which is assigned to a filter line $F_n^{(R)}$, is multiplied by the factor $1$, an intermediate filter value, which is assigned to a filter line $G_{n-2}^{(R)}$, is multiplied by the factor $\frac{1}{2}$, an intermediate filter value, which is assigned to a filter line $G_{n-2}^{(L)}$, is multiplied by the factor $-\frac{1}{2}$, and on forming a second filter value by linear combination of those intermediate filter values of the particular measured value which are assigned to the filter lines $F_1^{(R)}$, $F_3^{(R)}$, ..., $F_{n-2}^{(R)}$, $G_1^{(L)}$, $G_3^{(L)}$, ..., $G_{n-2}^{(L)}$, $G_3^{(R)}$, $G_5^{(R)}$, ..., $G_{n-2}^{(R)}$, an intermediate filter value, which is assigned to a filter line $F_1^{(R)}$, is multiplied by $n/3$, an intermediate filter value, which is assigned to a filter line $F_{n-2}^{(R)}$, is multiplied by $n/(n-2)$, an intermediate filter value, which is assigned to a filter line $F_k^{(R)}$, with $1<k<n-2$, is multiplied by $2n/(k(k+2))$, an intermediate filter value, which is assigned to a filter line $G_{n-2}^{(R)}$, is multiplied by $-n/(2(n-2))$, an intermediate filter value, which is assigned to a filter line $G_z^{(R)}$, with $z<n-2$, is multiplied by $-n/(z(z+2))$, an intermediate filter value, which is assigned to a filter line $G_{n-2}^{(L)}$, is multiplied by $n/(2(n-2))$, an intermediate filter value, which is assigned to a filter line $G_d^{(L)}$, with $d<n-2$, is multiplied by $n/(d(d+2))$.

12. Computed tomography method as claimed in claim 1, wherein, in step d), each filter value is determined from measured values that have been simultaneously acquired in step c), and in that when weighting filter values of one group in step e), a filter value of this group that has been determined from measured values that have been acquired whilst the object has moved more quickly, is weighted more weakly than a different filter value of this group that has been determined from measured values that have been acquired whilst the object has moved more slowly.

13. Computed tomography method as claimed in claim 1, wherein the object to be examined is a heart, in that during the acquisition in step c) simultaneously an electrocardiogram is recorded and in that when weighting filter values of one group in step e), a filter value of this group that has been determined from measured values that have been acquired whilst the heart was in the diastolic phase, is weighted more heavily than a different filter value of this group that has been determined from measured values that have been acquired whilst the heart was in the systolic phase.

14. Computer tomograph, especially for carrying out the method as claimed in claim 1, having a radiation source for generating a conical beam bundle passing through an examination zone and an object located therein, a drive arrangement, in order to cause an object located in the examination zone and the radiation source to rotate relative to one another about an axis of rotation and to be displaced parallel to the axis of rotation, a detector unit coupled to the radiation source, which detector unit has a detector surface for acquisition of measured values, a reconstruction unit for reconstructing a CT image of the examination zone from the measured values acquired by the detector unit, a control unit for controlling the radiation source, the detector unit, the drive arrangement and the reconstruction unit in conformity with the steps disclosed in claim 1.

15. Computer tomograph as claimed in claim 14, wherein the computer tomograph comprises means for recording the movement of the object, especially an electrocardiograph.

16. Computer program for a control unit for controlling a radiation source, a detector unit, a drive arrangement and a reconstruction unit of a computer tomograph as claimed in claim 14 for carrying out the method as claimed in claim 1.

* * * * *